United States Patent
Schulze et al.

(10) Patent No.: US 11,524,952 B2
(45) Date of Patent: Dec. 13, 2022

(54) COMPOUND AND ORGANIC SEMICONDUCTING LAYER, ORGANIC ELECTRONIC DEVICE, DISPLAY DEVICE AND LIGHTING DEVICE COMPRISING THE SAME

(71) Applicant: Novaled GmbH, Dresden (DE)

(72) Inventors: Benjamin Schulze, Dresden (DE); Francois Cardinali, Dresden (DE); Jerome Ganier, Dresden (DE); Volodymyr Senkovskyy, Dresden (DE)

(73) Assignee: Novaled GmbH, Dresden (DE)

( * ) Notice: Subject to any disclaimer, the term of this patent is extended or adjusted under 35 U.S.C. 154(b) by 602 days.

(21) Appl. No.: 16/387,645

(22) Filed: Apr. 18, 2019

(65) Prior Publication Data
US 2019/0322642 A1    Oct. 24, 2019

(30) Foreign Application Priority Data

Apr. 18, 2018  (EP) .................................. 18167970

(51) Int. Cl.
*H01L 51/50* (2006.01)
*C07D 401/10* (2006.01)
(Continued)

(52) U.S. Cl.
CPC ......... *C07D 401/10* (2013.01); *C07D 405/14* (2013.01); *H01L 51/0054* (2013.01);
(Continued)

(58) Field of Classification Search
None
See application file for complete search history.

(56) References Cited

U.S. PATENT DOCUMENTS

2005/0089715 A1*  4/2005  Cosimbescu ....... H01L 51/0052
428/690

FOREIGN PATENT DOCUMENTS

EP         3312899 A1      4/2018
KR      2015124000      * 11/2015    ............. H01L 51/50
(Continued)

OTHER PUBLICATIONS

European Search Report for EP Application No. 18167970 dated Sep. 26, 2018 (7 pages).

*Primary Examiner* — Gregory D Clark
(74) *Attorney, Agent, or Firm* — Eversheds Sutherland (US) LLP

(57) ABSTRACT

The present invention relates to a compound of the Formula (I)

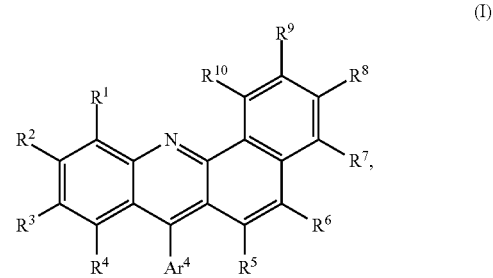

wherein at least one of $R^1$ to $R^{10}$ and/or $Ar^4$ is a group having the Formula (II)

(Continued)

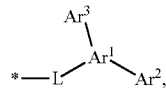

wherein the asterisk symbol "*" in Formula (II) represents the position of binding of the group having the Formula (II); L is selected from substituted or unsubstituted $C_6$ to $C_{18}$ arylene; $Ar^1$ is selected from substituted or unsubstituted $C_3$ to $C_{24}$ heteroaryl, wherein the heteroaryl comprises at least two N-atoms; $Ar^2$ and $Ar^3$ are independently selected from substituted or unsubstituted $C_6$ to $C_{24}$ aryl and/or substituted or unsubstituted $C_4$ to $C_{24}$ heteroaryl, wherein $Ar^2$ and $Ar^3$ are selected differently from each other; $Ar^4$ is selected from the group consisting of substituted or unsubstituted $C_1$ to $C_{16}$ alkyl, substituted or unsubstituted $C_6$ to $C_{24}$ aryl, substituted or unsubstituted $C_2$ to $C_{24}$ heteroaryl and a group having the general Formula (II); $R^1$ to $R^{10}$ are independently selected from the group consisting of H, D, F, $C_1$ to $C_{20}$ alkyl, $C_6$ to $C_{20}$ aryl, $C_2$ to $C_{20}$ heteroaryl and a group having the Formula (II); and $R^1$ and $R^2$; or $R^2$ and $R^3$ or $R^3$; and $R^4$; or $R^5$ and $R^6$ may independently from each other form a fused ring or system of fused rings; a semiconducting layer comprising the same, an organic electronic device comprising the same as well as a display or a lighting device comprising the organic electronic device.

17 Claims, 2 Drawing Sheets

(51) Int. Cl.
  *C07D 405/14* (2006.01)
  *H01L 51/00* (2006.01)
  *H01L 51/52* (2006.01)
(52) U.S. Cl.
  CPC ...... *H01L 51/0067* (2013.01); *H01L 51/0072* (2013.01); *H01L 51/0073* (2013.01); *H01L 51/5012* (2013.01); *H01L 51/5092* (2013.01); *H01L 51/5096* (2013.01); *H01L 51/5278* (2013.01); *H01L 51/001* (2013.01); *H01L 51/0079* (2013.01); *H01L 51/5056* (2013.01); *H01L 51/5072* (2013.01)

(56) References Cited

FOREIGN PATENT DOCUMENTS

| KR | 20160059336 A | | 5/2016 | |
| WO | 2015/083948 A1 | | 6/2015 | |
| WO | WO 2015/083948 | * | 6/2015 | ............. H01L 51/50 |

* cited by examiner

COMPOUND AND ORGANIC SEMICONDUCTING LAYER, ORGANIC ELECTRONIC DEVICE, DISPLAY DEVICE AND LIGHTING DEVICE COMPRISING THE SAME

CROSS REFERENCE TO RELATED APPLICATIONS

This application claims priority to European Patent Application No. 18167970.5, filed Apr. 18, 2018, which is incorporated herein by reference.

FIELD OF THE INVENTION

The present invention relates to a compound and an organic semiconducting layer comprising the same. The invention further relates to an organic electronic device comprising the organic semiconducting layer. Furthermore, the invention relates to a display device or a lighting device comprising the organic electronic device.

BACKGROUND ART

Organic light-emitting diodes (OLEDs), which are self-emitting devices, have a wide viewing angle, excellent contrast, quick response, high brightness, excellent driving voltage characteristics, and color reproduction. A typical OLED includes an anode, a hole transport layer (HTL), an emission layer (EML), an electron transport layer (ETL), and a cathode, which are sequentially stacked on a substrate. In this regard, the HTL, the EML, and the ETL are thin films formed from organic and/or organometallic compounds.

When a voltage is applied to the anode and the cathode, holes injected from the anode electrode move to the EML, via the HTL, and electrons injected from the cathode electrode move to the EML, via the ETL. The holes and electrons recombine in the EML to generate excitons. When the excitons drop from an excited state to a ground state, light is emitted. The injection and flow of holes and electrons should be balanced, so that an OLED having the above-described structure has excellent efficiency.

EP 3 312 899 A1 relates to an organic light-emitting diode (OLED) including an ETL stack of at least two electron transport layers, wherein the first electron transport layer (135) comprises a charge transporting compound and the second electron transport layer (34) comprises an acridine compound and an alkali metal salt and/or alkali metal organic complex, a method of manufacturing the same and a device comprising the OLED.

WO 2015/083948 A1 provides: a novel compound capable of improving the luminous efficiency, stability and lifetime of an element; an organic electric element using the same; and an electronic device thereof.

KR 2016 0059 336 A provides: a compound which has high light-emitting efficiency of an element and low driving voltage of an element, and is capable of improving lifespan of an element; an organic electronic element using the same; and an electronic device thereof. In addition, the compound is represented by chemical formula 1

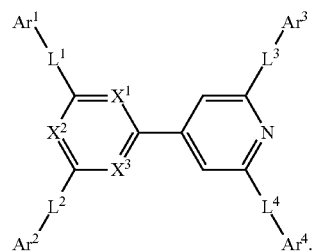

Acridine compounds which are symmetrically substituted on a heteroaryl comprised therein are used in organic electronics applications, especially as electron transport materials. Respective compounds often have very high melting points and no measurable glass transition temperature (Tg). Without being bound by theory, a very high melting point combined with a lack of Tg may be indicative of a compound with high crystallinity. High crystallinity is not preferred in applications in organic electronics, as crystallization may be detrimental to conductivity and morphological stability of an organic semiconducting layer. In particular, in an organic semiconducting layer further comprising a dopant, high crystallinity of the matrix compound may result in de-mixing of the composition. Furthermore, there is still a need to improve the electronic properties of respective compounds for use in organic electronic devices, in particular to provide compounds having a less negative LUMO.

It is therefore an object of the present invention to provide novel organic electronic devices and compounds for use therein overcoming drawbacks of the prior art, in particular to provide novel compounds having improved morphological properties, in particular melting points and/or glass transition temperatures and/or electronic properties which may be suitable to improve the performance of organic electronic devices, in particular when used in an electron transport layer.

The above object is achieved by a compound of the Formula (I)

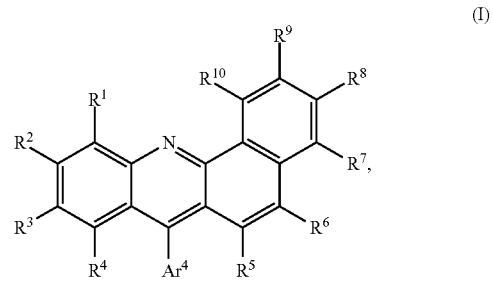

wherein at least one of $R^1$ to $R^{10}$ and/or $Ar^4$ is a group having the Formula (II)

wherein the asterisk symbol "*" in Formula (II) represents the position of binding of the group having the Formula (II);

L is selected from substituted or unsubstituted $C_6$ to $C_{18}$ arylene;

$Ar^1$ is selected from the group consisting of substituted or unsubstituted $C_3$ to $C_{24}$ heteroaryl, wherein the heteroaryl comprises at least two N-atoms;

$Ar^2$ and $Ar^3$ are independently selected from the group consisting of substituted or unsubstituted $C_6$ to $C_{24}$ aryl and/or substituted or unsubstituted $C_4$ to $C_{24}$ heteroaryl, wherein $Ar^2$ and $Ar^3$ are selected differently from each other;

$Ar^4$ is selected from the group consisting of substituted or unsubstituted $C_1$ to $C_{16}$ alkyl, substituted or unsubstituted $C_6$ to $C_{24}$ aryl, substituted or unsubstituted $C_2$ to $C_{24}$ heteroaryl, and a group having the general Formula (II);

$R^1$ to $R^{10}$ are independently selected from the group consisting of H, D, F, $C_1$ to $C_{20}$ alkyl, $C_6$ to $C_{20}$ aryl, $C_2$ to $C_{20}$ heteroaryl and a group having the Formula (II); and $R^1$ and $R^2$; or $R^2$ and $R^3$; or $R^3$ and $R^4$; or $R^5$ and $R^6$ may independently from each other form a fused ring or a system of fused rings;

wherein, in the respective substituted groups, the substituents each are independently selected from the group consisting of D, F, $C_1$ to $C_{20}$ linear alkyl, $C_3$ to $C_{20}$ branched alkyl, $C_3$ to $C_{20}$ cyclic alkyl, $C_1$ to $C_{20}$ linear alkoxy, $C_3$ to $C_{20}$ branched alkoxy, $C_1$ to $C_{12}$ linear fluorinated alkyl, $C_1$ to $C_{12}$ linear fluorinated alkoxy, $C_3$ to $C_{12}$ branched fluorinated cyclic alkyl, $C_3$ to $C_{20}$ fluorinated cyclic alkyl, $C_3$ to $C_{12}$ fluorinated cyclic alkoxy, CN, RCN, $C_6$ to $C_{20}$ aryl, $C_2$ to $C_{20}$ heteroaryl, OR, SR, (C=O)R, (C=O)NR$_2$, SiR$_3$, (S=O)R, (S=O)$_2$R, (P=O)R$_2$; wherein each R is independently selected from the group consisting of $C_1$ to $C_{20}$ linear alkyl, $C_1$ to $C_{20}$ alkoxy, $C_1$ to $C_{20}$ thioalkyl, $C_3$ to $C_{20}$ branched alkyl, $C_3$ to $C_{20}$ cyclic alkyl, $C_3$ to $C_{20}$ branched alkoxy, $C_3$ to $C_{20}$ cyclic alkoxy, $C_3$ to $C_{20}$ branched thioalkyl, $C_3$ to $C_{20}$ cyclic thioalkyl, $C_6$ to $C_{20}$ aryl and $C_2$ to $C_{20}$ heteroaryl.

In the above Formula, the single bond between the benzoacridine moiety and the respective R'', respectively $Ar^4$, group is the same single bond as that between the asteric symbol "*" and the moiety L.

$Ar^2$ and $Ar^3$ are selected differently from each other. That is, that $Ar^2$ and $Ar^3$ are chemically not identical. In other words, both groups are selected from substituted or unsubstituted $C_6$ to $C_{24}$ aryl or substituted or unsubstituted $C_4$ to $C_{24}$ heteroaryl but the selected group cannot be the same for $Ar^2$ and $Ar^3$. Compounds in which $Ar^2$ and $Ar^3$ are selected the same (not according to the invention and known from the prior art) are designated herein as "symmetrically substituted". Inventive compounds in which $Ar^2$ and $Ar^3$ are selected differently from each other are designated as "asymmetrically substituted".

It has surprisingly been found by the inventors that asymmetrically substituted compounds of Formula (I) have favorable melting points, glass transition temperatures, rate onset temperatures and/or electronic properties, in particular feature a less negative LUMO which improves the usability thereof in organic semiconducting materials and organic electronic devices.

With respect to the compound of Formula (I) it may be provided that one or more of the compounds respectively by following Formulas are excluded:

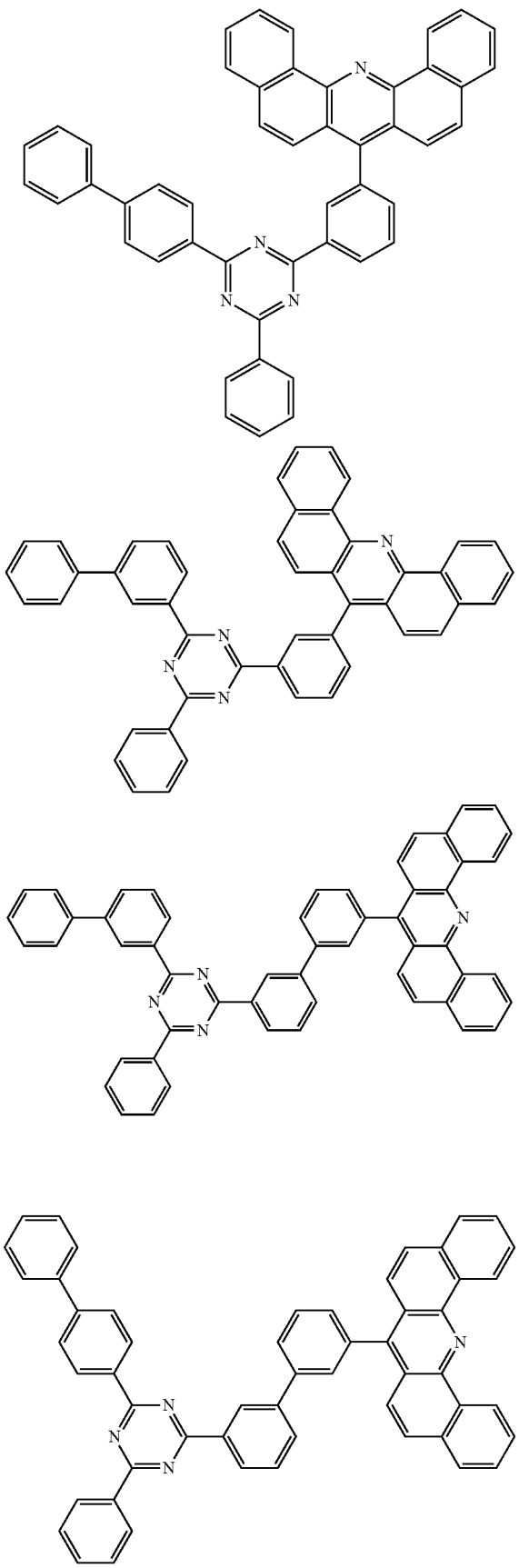

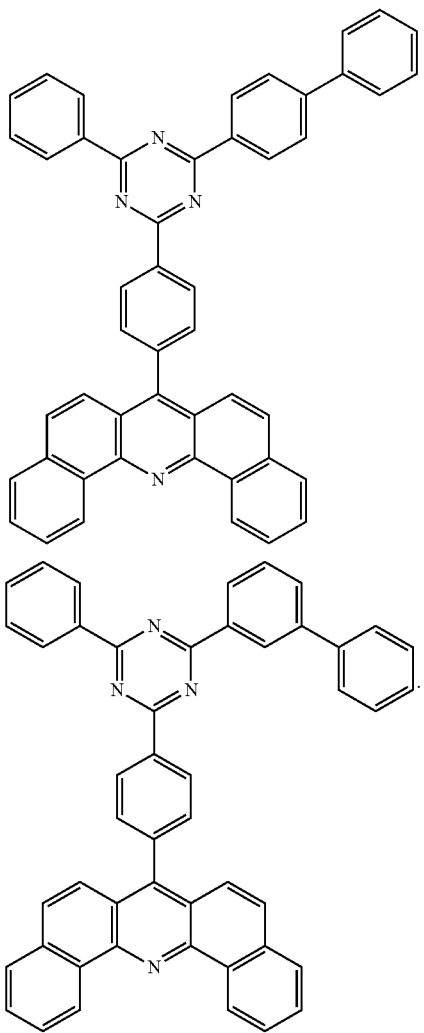

In the inventive compound L may be selected from the group consisting of phenylene, biphenylene, terphenylene, phenanthrylene, triphenylylene and naphthylene; alternatively from the group consisting of phenylene, biphenylene and naphthylene; alternatively from the group consisting of phenylene and biphenylene. In this way, fine tuning of the thermal properties and electronic structure of the compound of Formula (I) can be achieved to further improve the usability thereof in organic semiconducting layers of organic electronic devices in particular in electron transport layers.

In the inventive compound $Ar^1$ may be selected from triazine and pyrimidine. Alternatively, $Ar^1$ may be selected from triazine, pyrazine and pyrimidine. In this way, fine tuning of the electronic structure of the compound of Formula (I) can be achieved to further improve the usability thereof in organic semiconducting layers of organic electronic devices in particular in electron transport layers.

$Ar^1$ may be free of carbazole and/or indolocarbazole groups.

In the inventive compound $Ar^3$ may be biphenyl, naphthyl, dibenzofuranyl or dibenzothiophenyl; alternatively $Ar^3$ may be selected from the following groups having the Formulas (III) and (IV)

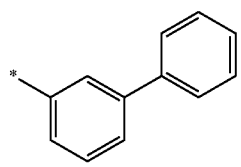

(III)

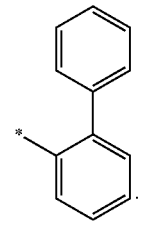

(IV)

In this way, fine tuning of the electronic structure of the compound of Formula (I) can be achieved to further improve the usability thereof in organic semiconducting layers of organic electronic devices in particular in electron transport layers.

In the inventive compound, $Ar^3$ may be substituted phenyl or biphenyl, wherein the substituent on $Ar^3$ is selected differently from the substituent on $Ar^2$, if present. The substituent on $Ar^3$ may be selected from CN. Alternatively, $Ar^3$ is selected from $—C_6H_5CN$.

In the inventive compound $Ar^3$ may be biphenyl, naphthyl, dibenzofuranyl or dibenzothiophenyl, substituted phenyl or substituted biphenyl; alternatively $Ar^3$ may be selected from the following groups having the Formulas (III), (IV), (V) and (VI)

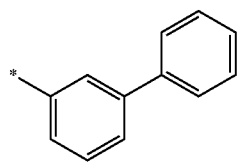

(III)

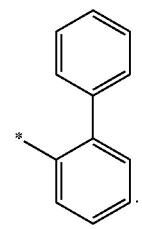

(IV)

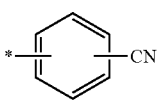

(V)

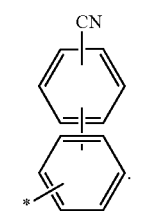

(VI)

In this way, fine tuning of the electronic structure of the compound of Formula (I) can be achieved to further improve the usability thereof in organic semiconducting layers of organic electronic devices in particular in electron transport layers.

In the inventive compound, $Ar^1$ may be triazine, pyrazine or pyrimidine and $Ar^3$ may be selected from Formulas (III) to (VI); alternatively, $Ar^1$ may be pyrimidine and $Ar^3$ may be selected from Formulas (III) to (VI). In this way, fine tuning of the electronic structure of the compound of Formula (I) can be achieved to further improve the usability thereof in organic semiconducting layers of organic electronic devices in particular in electron transport layers. In the inventive compound $Ar^2$ may be phenyl. In this way, fine tuning of the electronic structure of the compound of Formula (I) can be achieved to further improve the usability thereof in organic semiconducting layers of organic electronic devices in particular in electron transport layers.

In the inventive compound, it may be provided that $Ar^2$ is phenyl and $Ar^3$ is biphenyl or —$C_6H_5CN$. In this way, fine tuning of the electronic structure of the compound of Formula (I) can be achieved to further improve the usability thereof in organic semiconducting layers of organic electronic devices in particular in electron transport layers.

In the inventive compound $Ar^4$ may be selected from the group consisting of phenyl, biphenyl, terphenyl and naphthyl and a group having the Formula (II); alternatively $Ar^4$ is selected from Formula (II). In this way, fine tuning of the morphological properties and electronic structure of the compound of Formula (I) can be achieved to further improve the usability thereof in organic semiconducting layers of organic electronic devices in particular in electron transport layers.

In the inventive compound $Ar^4$ may be selected from the group consisting of phenyl, biphenyl, terphenyl and naphthyl and $R^1$ to $R^{10}$, alternatively $R^9$, are independently selected from the group consisting of H, D and a group having the Formula (II). In this way, fine tuning of the morphological properties and electronic structure of the compound of Formula (I) can be achieved to further improve the usability thereof in organic semiconducting layers of organic electronic devices in particular in electron transport layers.

In the inventive compound $R^1$ and $R^2$ may form together a fused ring, alternatively $R^1$ and $R^2$ form together a six-membered fused ring. In this way, fine tuning of the morphological properties and electronic structure of the compound of Formula (I) can be achieved to further improve the usability thereof in organic semiconducting layers of organic electronic devices in particular in electron transport layers.

The inventive compound of Formula (I) may have one of the following Formulas (Ia), (Ib), (Ic) and (Id)

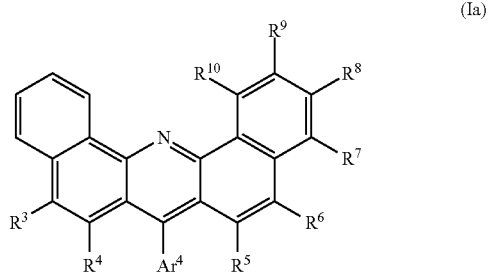
(Ia)

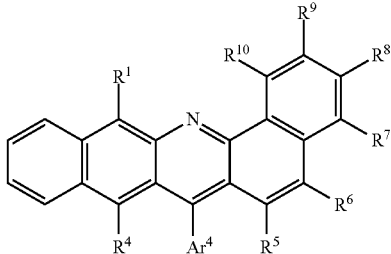
(Ib)

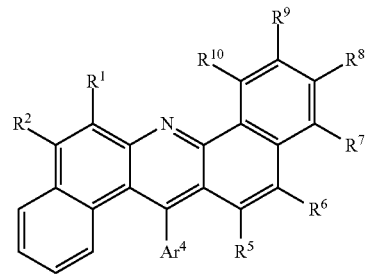
(Ic)

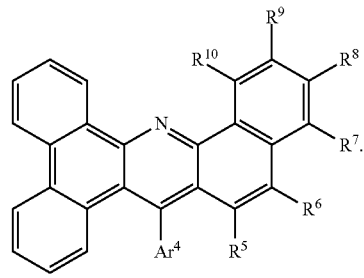
(Id)

In this way, fine tuning of the morphological properties and electronic structure of the compound of Formula (I) can be achieved to further improve the usability thereof in organic semiconducting layers of organic electronic devices in particular in electron transport layers.

L, $Ar^1$, $Ar^2$ and $Ar^3$ may be unsubstituted. Thereby, particularly beneficial performance in organic electronic devices may be obtained, when the compound of formula (I) is evaporated and deposited on the substrate in high vacuum.

Compound of Formula (I) may have one of the Formulas (Ia), (Ib), (Ic) and (Id), wherein $R^1$ to $R^{10}$ are H and $Ar^4$ is selected from Formula (II). Preferably, compound of Formula (I) may have Formula (Ia), wherein $R^3$ to $R^{10}$ are H and $Ar^4$ is selected from Formula (II).

In the compound of Formula (I) $R^1$ to $R^{10}$ may be H and $Ar^4$ may be Formula (II).

The inventive compound may have one of the following structures A-1 to A-15
A-1
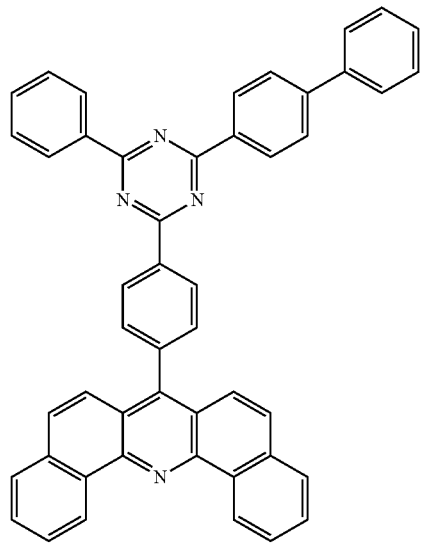 [SMILES: c1ccc(-c2ccc(-c3nc(-c4ccccc4)nc(-c4ccc(-c5c6ccc7ccccc7c6nc6c5ccc5ccccc56)cc4)n3)cc2)cc1]
A-2
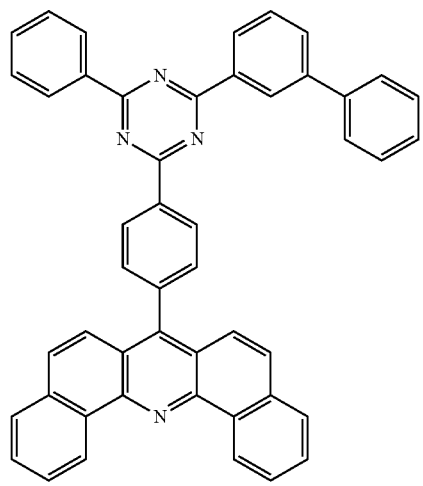 [SMILES: c1ccc(-c2cccc(-c3nc(-c4ccccc4)nc(-c4ccc(-c5c6ccc7ccccc7c6nc6c5ccc5ccccc56)cc4)n3)c2)cc1]
A-3
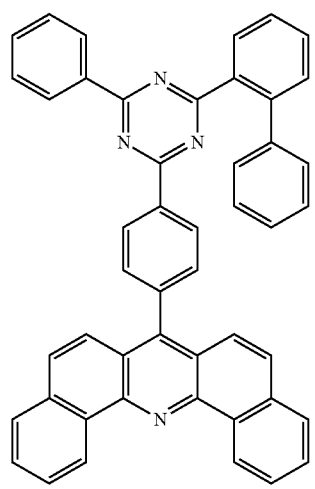 [SMILES: c1ccc(-c2nc(-c3ccc(-c4c5ccc6ccccc6c5nc5c4ccc4ccccc45)cc3)nc(-c3ccccc3-c3ccccc3)n2)cc1]
A-4
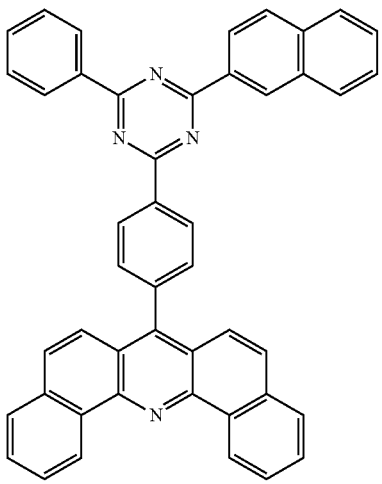
A-5
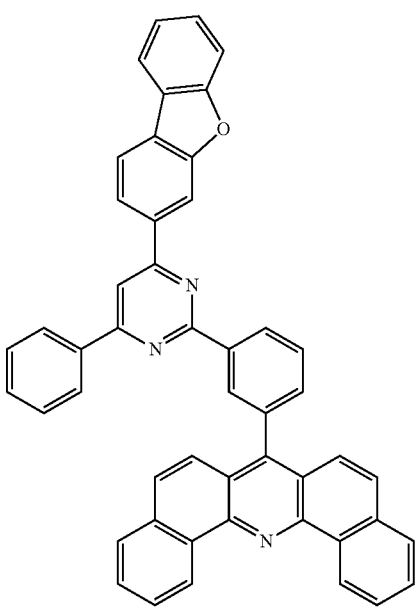
A-6
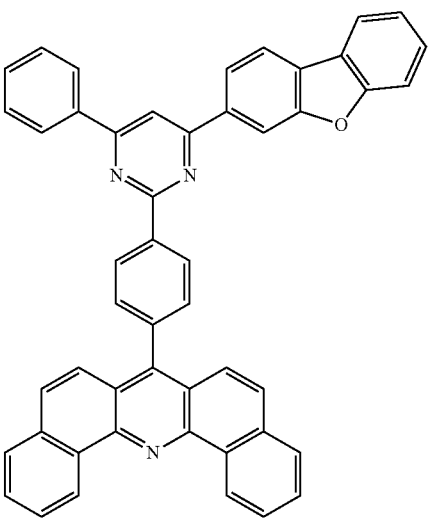

A-7
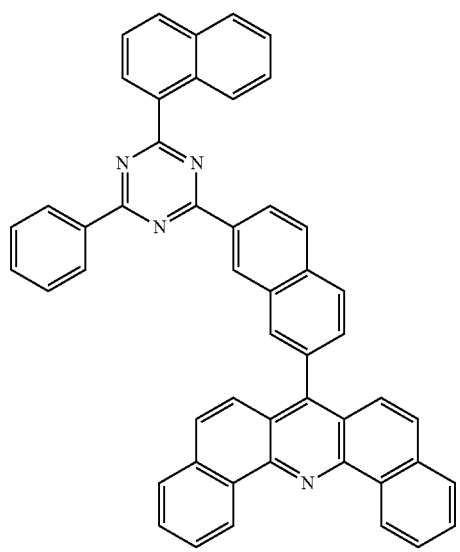
A-8
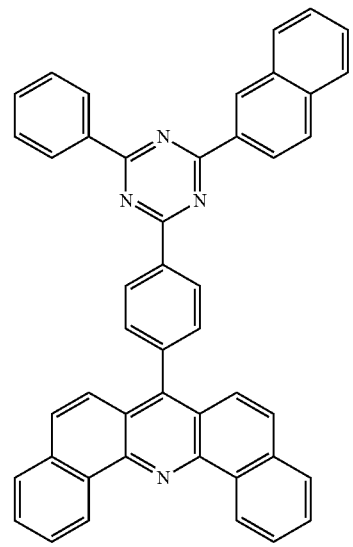
A-9
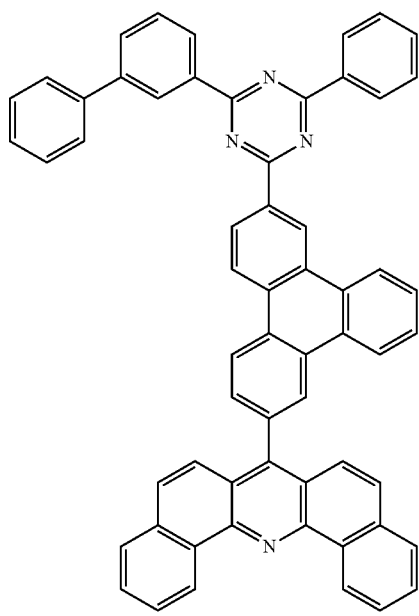
A-10
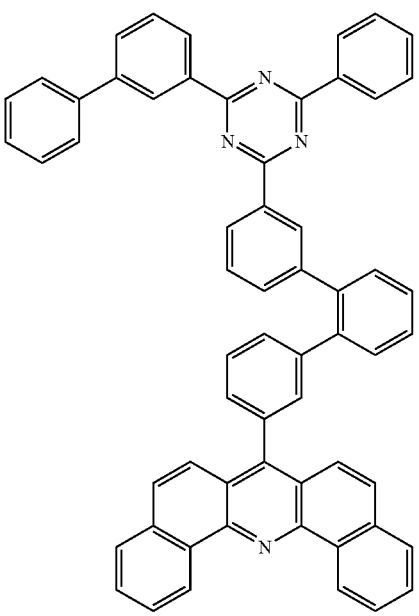

A-11

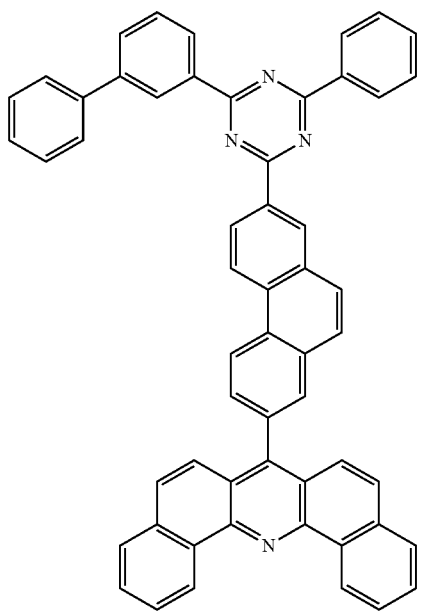

A-12

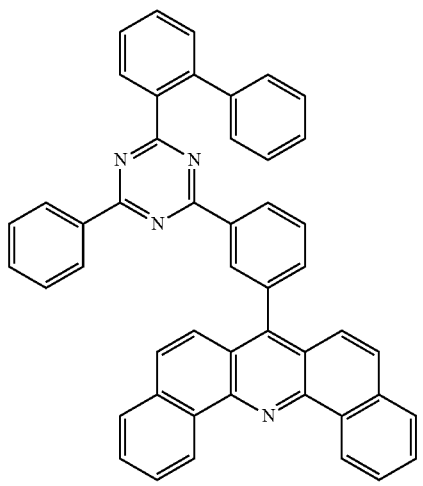 [SMILES: c1ccc(-c2nc(-c3cccc(-c4c5ccc6ccccc6c5nc5c4ccc4ccccc45)c3)nc(-c3ccccc3-c3ccccc3)n2)cc1]

A-13

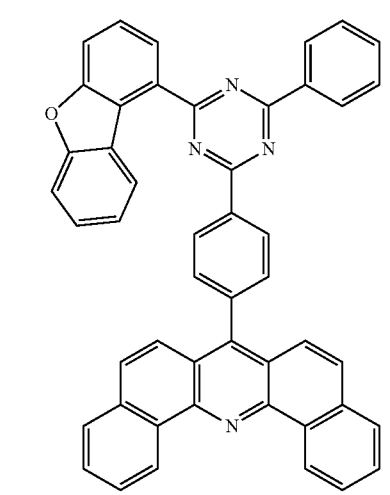

A-14

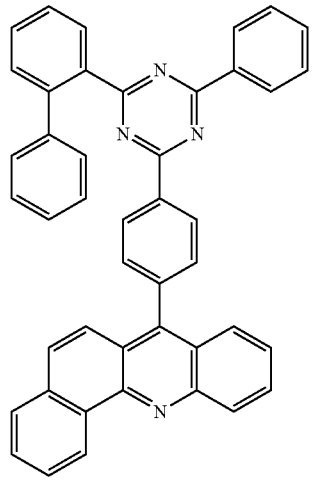

A-15

In this way, fine tuning of the morphological properties and electronic structure of the compound of Formula (I) can be achieved to further improve the usability thereof in organic semiconducting layers of organic electronic devices in particular in electron transport layers.

The object is further achieved by an organic semiconducting layer comprising the inventive compound of Formula (I).

The organic semiconducting layer may consist of a compound of Formula (I).

The organic semiconducting layer comprising or consisting of the compound of Formula (I) may be non-emissive.

The organic semiconducting layer may further comprise a metal, a metal salt or an alkali or alkaline earth metal complex; alternatively an organic alkali or alkaline earth metal complex; alternatively 8-hydroxyquinolinolato lithium or alkali borate. Additionally, the object is achieved by an organic electronic device comprising the inventive organic semiconducting layer.

The organic electronic device comprising the inventive organic semiconducting layer may further comprise an anode, a cathode and an emission layer.

In the organic electronic device, the organic semiconducting layer comprising compound of Formula (I) may be arranged between the anode and the cathode.

The organic semiconducting layer may be arranged between the emission layer and the cathode. If the organic semiconducting layer is arranged in this way, it may function as electron transport layer.

In the organic electronic device, the organic semiconducting layer may be in direct contact with the emission layer.

The organic electronic device may further comprise a hole blocking layer, wherein the hole blocking layer is in direct contact with the emission layer and the organic semiconductor layer comprising the compound of Formula (I) is arranged between the hole blocking layer and the cathode.

The organic semiconducting layer may be arranged between the hole blocking layer and the cathode and may be in direct contact with the hole blocking layer and the cathode.

In the organic electronic device, the organic semiconducting layer may further comprise a metal, a metal salt or an alkali or alkaline earth metal complex, alternatively an organic alkali or alkaline earth metal complex, alternatively 8-hydroxyquinolinolato-lithium or an alkali borate.

The object is further achieved by an organic semiconducting material comprising a compound of Formula (I)

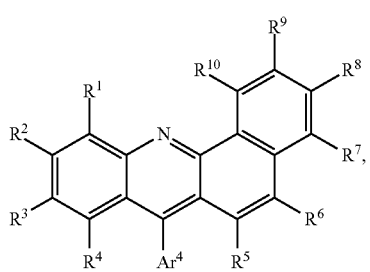

(I)

wherein at least one of $R^1$ to $R^{10}$ and/or $Ar^4$ is a group having the Formula (II)

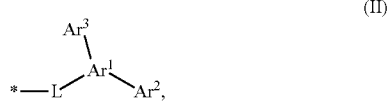

(II)

wherein the asterisk symbol "*" in Formula (II) represents the position of binding of the group having the Formula (II);

L is selected from substituted or unsubstituted $C_6$ to $C_{18}$ arylene;

$Ar^1$ is selected from substituted or unsubstituted $C_3$ to $C_{24}$ heteroaryl, wherein the heteroaryl comprises at least two N-atoms;

$Ar^2$ and $Ar^3$ are independently selected from substituted or unsubstituted $C_6$ to $C_{24}$ aryl and/or substituted or unsubstituted $C_4$ to $C_{24}$ heteroaryl, wherein $Ar^2$ and $Ar^3$ are selected differently from each other;

$Ar^4$ is selected from the group consisting of substituted or unsubstituted $C_1$ to $C_{16}$ alkyl, substituted or unsubstituted $C_6$ to $C_{24}$ aryl, substituted or unsubstituted $C_2$ to $C_{24}$ heteroaryl and a group having the general Formula (II);

$R^1$ to $R^{10}$ are independently selected from the group consisting of H, D, F, $C_1$ to $C_{20}$ alkyl, $C_6$ to $C_{20}$ aryl, $C_2$ to $C_{20}$ heteroaryl and a group having the Formula (II); and $R^1$ and $R^2$; or $R^2$ and $R^3$; or $R^3$ and $R^4$; or $R^5$ and $R^6$ may independently from each other form a fused ring or a system of fused rings;

wherein, in the respective substituted groups, the substituents each are independently selected from the group consisting of D, F, $C_1$ to $C_{20}$ linear alkyl, $C_3$ to $C_{20}$ branched alkyl, $C_3$ to $C_{20}$ cyclic alkyl, $C_1$ to $C_{20}$ linear alkoxy, $C_3$ to $C_{20}$ branched alkoxy, $C_1$ to $C_{12}$ linear fluorinated alkyl, $C_1$ to $C_{12}$ linear fluorinated alkoxy, $C_3$ to $C_{12}$ branched fluorinated cyclic alkyl, $C_3$ to $C_{20}$ fluorinated cyclic alkyl, $C_3$ to $C_{12}$ fluorinated cyclic alkoxy, CN, RCN, $C_6$ to $C_{20}$ aryl, $C_2$ to $C_{20}$ heteroaryl, OR, SR, (C=O)R, (C=O)NR$_2$, SiR$_3$, (S=O)R, (S=O)$_2$R, (P=O)R$_2$; wherein each R is independently selected from the group consisting of $C_1$ to $C_{20}$ linear alkyl, $C_1$ to $C_{20}$ alkoxy, $C_1$ to $C_{20}$ thioalkyl, $C_3$ to $C_{20}$ branched alkyl, $C_3$ to $C_{20}$ cyclic alkyl, $C_3$ to $C_{20}$ branched alkoxy, $C_3$ to $C_{20}$ cyclic alkoxy, $C_3$ to $C_{20}$ branched thioalkyl, $C_3$ to $C_{20}$ cyclic thioalkyl, $C_6$ to $C_{20}$ aryl and $C_2$ to $C_{20}$ heteroaryl; and a metal, a metal salt or an alkali or alkaline earth metal complex; alternatively an organic alkali or alkaline earth metal complex; alternatively 8-hydroxyquinolinolato lithium or alkali borate.

The object is further achieved by an organic semiconducting layer comprising the organic semiconducting material.

The organic semiconducting layer comprising or consisting of the organic semiconducting material may be non-emissive.

Additionally, the object is achieved by an organic electronic device comprising the inventive organic semiconducting layer comprising the organic semiconducting material.

The organic electronic device comprising the inventive organic semiconducting layer comprising the organic semiconducting material may further comprise an anode, a cathode and an emission layer.

In the organic electronic device, the organic semiconducting layer comprising the organic semiconducting material may be arranged between the anode and the cathode.

The organic semiconducting layer comprising the organic semiconducting material may be arranged between the emission layer and the cathode. If the organic semiconducting layer is arranged in this way, it may function as electron transport layer.

The organic electronic device may further comprise a hole blocking layer, wherein the hole blocking layer is in direct contact with the emission layer and the organic semiconductor layer comprising the organic semiconducting material is arranged between the hole blocking layer and the cathode.

The organic semiconducting layer comprising the organic semiconducting material may be arranged between the hole blocking layer and the cathode and may be in direct contact with the hole blocking layer and the cathode.

Furthermore, the object is achieved by a display device comprising the inventive organic electronic device.

Finally, the object is achieved by a lighting device comprising the inventive organic electronic device.

In accordance with the invention, the structures shown in table 1 below are most preferred.

Further Layers

In accordance with the invention, the organic electronic device may comprise, besides the layers already mentioned above, further layers. Exemplary embodiments of respective layers are described in the following:

Substrate

The substrate may be any substrate that is commonly used in manufacturing of, electronic devices, such as organic light-emitting diodes. If light is to be emitted through the substrate, the substrate shall be a transparent or semitransparent material, for example a glass substrate or a transparent plastic substrate. If light is to be emitted through the top surface, the substrate may be both a transparent as well as a non-transparent material, for example a glass substrate, a plastic substrate, a metal substrate or a silicon substrate.

Anode Electrode

Either a first electrode or a second electrode comprised in the inventive organic electronic device may be an anode electrode. The anode electrode may be formed by depositing or sputtering a material that is used to form the anode electrode. The material used to form the anode electrode may be a high work-function material, so as to facilitate hole injection. The anode material may also be selected from a low work function material (i.e. aluminum). The anode electrode may be a transparent or reflective electrode. Transparent conductive oxides, such as indium tin oxide (ITO), indium zinc oxide (IZO), tin-dioxide (SnO2), aluminum zinc oxide (AlZO) and zinc oxide (ZnO), may be used to form the anode electrode. The anode electrode may also be formed using metals, typically silver (Ag), gold (Au), or metal alloys.

Hole Injection Layer

A hole injection layer (HIL) may be formed on the anode electrode by vacuum deposition, spin coating, printing, casting, slot-die coating, Langmuir-Blodgett (LB) deposition, or the like. When the HIL is formed using vacuum deposition, the deposition conditions may vary according to the compound that is used to form the HIL, and the desired structure and thermal properties of the HIL. In general, however, conditions for vacuum deposition may include a deposition temperature of 100° C. to 500° C., a pressure of 10-8 to 10-3 Torr (1 Torr equals 133.322 Pa), and a deposition rate of 0.1 to 10 nm/sec.

When the HIL is formed using spin coating or printing, coating conditions may vary according to the compound that is used to form the HIL, and the desired structure and thermal properties of the HIL. For example, the coating conditions may include a coating speed of about 2000 rpm to about 5000 rpm, and a thermal treatment temperature of about 80° C. to about 200° C. Thermal treatment removes a solvent after the coating is performed.

The HIL may be formed of any compound that is commonly used to form a HIL. Examples of compounds that may be used to form the HIL include a phthalocyanine compound, such as copper phthalocyanine (CuPc), 4,4',4"-tris (3-methylphenylphenylamino) triphenylamine (m-MTDATA), TDATA, 2T-NATA, polyaniline/dodecylbenzene-sulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS).

The HIL may comprise or consist of p-type dopant and the p-type dopant may be selected from tetrafluoro-tetracyano-quinonedimethane (F4TCNQ), 2,2'-(perfluoronaphthalen-2,6-diylidene) dimalononitrile or 2,2',2"-(cyclopropane-1,2,3-triylidene)tris(2-(p-cyanotetrafluorophenyl)acetonitrile) but not limited hereto. The HIL may be selected from a hole-transporting matrix compound doped with a p-type dopant. Typical examples of known doped hole transport materials are: copper phthalocyanine (CuPc), which HOMO level is approximately −5.2 eV, doped with tetrafluoro-tetracyano-quinonedimethane (F4TCNQ), which LUMO level is about −5.2 eV; zinc phthalocyanine (ZnPc) (HOMO=−5.2 eV) doped with F4TCNQ; α-NPD (N,N'-Bis(naphthalen-1-yl)-N,N'-bis(phenyl)-benzidine) doped with F4TCNQ. α-NPD doped with 2,2'-(perfluoronaphthalen-2,6-diylidene) dimalononitrile. The p-type dopant concentrations can be selected from 1 to 20 wt.-%, more preferably from 3 wt.-% to 10 wt.-%.

The thickness of the HIL may be in the range from about 1 nm to about 100 nm, and for example, from about 1 nm to about 25 nm. When the thickness of the HIL is within this range, the HIL may have excellent hole injecting characteristics, without a substantial penalty in driving voltage.

Hole Transport Layer

A hole transport layer (HTL) may be formed on the HIL by vacuum deposition, spin coating, slot-die coating, printing, casting, Langmuir-Blodgett (LB) deposition, or the like. When the HTL is formed by vacuum deposition or spin coating, the conditions for deposition and coating may be similar to those for the formation of the HIL. However, the conditions for the vacuum or solution deposition may vary, according to the compound that is used to form the HTL.

The HTL may be formed of any compound that is commonly used to form a HTL. Compounds that can be suitably used are disclosed for example in Yasuhiko Shirota and Hiroshi Kageyama, Chem. Rev. 2007, 107, 953-1010 and incorporated by reference. Examples of the compound that may be used to form the HTL are: carbazole derivatives, such as N-phenylcarbazole or polyvinylcarbazole; benzidine derivatives, such as N,N'-bis(3-methylphenyl)-N,N'-diphenyl-[1,1-biphenyl]-4,4'-diamine (TPD), or N,N'-di(naphthalen-1-yl)-N,N'-diphenyl benzidine (alpha-NPD); and triphenylamine-based compound, such as 4,4',4"-tris(N-carbazolyl)triphenylamine (TCTA). Among these compounds, TCTA can transport holes and inhibit excitons from being diffused into the EML.

The thickness of the HTL may be in the range of about 5 nm to about 250 nm, preferably, about 10 nm to about 200 nm, further about 20 nm to about 190 nm, further about 40 nm to about 180 nm, further about 60 nm to about 170 nm, further about 80 nm to about 160 nm, further about 100 nm to about 160 nm, further about 120 nm to about 140 nm. A preferred thickness of the HTL may be 170 nm to 200 nm.

When the thickness of the HTL is within this range, the HTL may have excellent hole transporting characteristics, without a substantial penalty in driving voltage.

Electron Blocking Layer

The function of an electron blocking layer (EBL) is to prevent electrons from being transferred from an emission layer to the hole transport layer and thereby confine electrons to the emission layer. Thereby, efficiency, operating voltage and/or lifetime are improved. Typically, the electron blocking layer comprises a triarylamine compound. The triarylamine compound may have a LUMO level closer to vacuum level than the LUMO level of the hole transport layer. The electron blocking layer may have a HOMO level that is further away from vacuum level compared to the HOMO level of the hole transport layer. The thickness of the electron blocking layer may be selected between 2 and 20 nm.

If the electron blocking layer has a high triplet level, it may also be described as triplet control layer.

The function of the triplet control layer is to reduce quenching of triplets if a phosphorescent green or blue emission layer is used. Thereby, higher efficiency of light emission from a phosphorescent emission layer can be achieved. The triplet control layer is selected from triarylamine compounds with a triplet level above the triplet level of the phosphorescent emitter in the adjacent emission layer. Suitable compounds for the triplet control layer, in particular the triarylamine compounds, are described in EP 2 722 908 A1.

Emission Layer (EML)

The EML may be formed on the HTL by vacuum deposition, spin coating, slot-die coat-ing, printing, casting, LB deposition, or the like. When the EML is formed using vacuum deposition or spin coating, the conditions for deposition and coating may be similar to those for the formation of the HIL. However, the conditions for deposition and coating may vary, according to the compound that is used to form the EML.

It may be provided that the emission layer does not comprise the compound of Formula (I).

The emission layer (EML) may be formed of a combination of a host and an emitter dopant. Example of the host are Alq3, 4,4'-N,N'-dicarbazole-biphenyl (CBP), poly(n-vinylcarbazole) (PVK), 9,10-di(naphthalene-2-yl)anthracene (ADN), 4,4',4''-tris(carbazol-9-yl)-triphenylamine(TCTA), 1,3,5-tris(N-phenylbenzimidazole-2-yl)benzene (TPBI), 3-tert-butyl-9,10-di-2-naphthylanthracenee (TBADN), distyrylarylene (DSA) and bis(2-(2-hydroxyphenyl)benzothiazolate)zinc (Zn(BTZ)2).

The emitter dopant may be a phosphorescent or fluorescent emitter. Phosphorescent emitters and emitters which emit light via a thermally activated delayed fluorescence (TADF) mechanism may be preferred due to their higher efficiency. The emitter may be a small molecule or a polymer.

Examples of red emitter dopants are PtOEP, Ir(piq)3, and Btp2Ir(acac), but are not limited thereto. These compounds are phosphorescent emitters, however, fluorescent red emitter dopants could also be used.

Examples of phosphorescent green emitter dopants are Ir(ppy)3 (ppy=phenylpyridine), Ir(ppy)2(acac), Ir(mpyp)3.

Examples of phosphorescent blue emitter dopants are F2Irpic, (F2ppy)2Ir(tmd) and Ir(dfppz)3 and ter-fluorene. 4.4'-bis(4-diphenyl amiostyryl)biphenyl (DPAVBi), 2,5,8,11-tetra-tert-butyl perylene (TBPe) are examples of fluorescent blue emitter dopants.

The amount of the emitter dopant may be in the range from about 0.01 to about 50 parts by weight, based on 100 parts by weight of the host. Alternatively, the emission layer may consist of a light-emitting polymer. The EML may have a thickness of about 10 nm to about 100 nm, for example, from about 20 nm to about 60 nm. When the thickness of the EML is within this range, the EML may have excellent light emission, without a substantial penalty in driving voltage.

Hole Blocking Layer (HBL)

A hole blocking layer (HBL) may be formed on the EML, by using vacuum deposition, spin coating, slot-die coating, printing, casting, LB deposition, or the like, in order to prevent the diffusion of holes into the ETL. When the EML comprises a phosphorescent dopant, the HBL may have also a triplet exciton blocking function. The hole blocking layer may be the inventive organic semiconducting layer comprising or consisting of the inventive compound represented by the general Formula (I) as defined above.

The HBL may also be named auxiliary ETL or a-ETL.

When the HBL is formed using vacuum deposition or spin coating, the conditions for deposition and coating may be similar to those for the formation of the HIL. However, the conditions for deposition and coating may vary, according to the compound that is used to form the HBL. Any compound that is commonly used to form a HBL may be used. Examples of compounds for forming the HBL include oxadiazole derivatives, triazole derivatives, and phenanthroline derivatives.

The HBL may have a thickness in the range from about 5 nm to about 100 nm, for example, from about 10 nm to about 30 nm. When the thickness of the HBL is within this range, the HBL may have excellent hole-blocking properties, without a substantial penalty in driving voltage.

Electron Transport Layer (ETL)

The OLED according to the present invention may comprise an electron transport layer (ETL). In accordance with the invention, the electron transport layer may be the inventive organic semiconducting layer comprising the inventive compound represented by the general Formula (I) as defined above.

According to various embodiments the OLED may comprise an electron transport layer or an electron transport layer stack comprising at least a first electron transport layer and at least a second electron transport layer.

By suitably adjusting energy levels of particular layers of the ETL, the injection and transport of the electrons may be controlled, and the holes may be efficiently blocked. Thus, the OLED may have long lifetime.

The electron transport layer of the organic electronic device may comprise the compound represented by general Formula (I) as defined above as the organic electron transport matrix (ETM) material. The electron transport layer may comprise, besides the compound represented by the general Formula (I), further ETM materials known in the art. Likewise, the electron transport layer may comprise as the only electron transport matrix material the compound represented by general Formula (I). In case that the inventive organic electronic device comprises more than one electron transport layers, the compound represented by the general Formula (I) may be comprised in only one of the electron transport layers, in more than one of the electron transport layers or in all of the electron transport layers. In accordance with the invention, the electron transport layer may comprise, besides the ETM material, at least one additive as defined below.

Further, the electron transport layer may comprise one or more n-type dopants. The additive may be an n-type dopant. The additive can be alkali metal, alkali metal compound, alkaline earth metal, alkaline earth metal compound, transition metal, transition metal compound or a rare earth metal. In another embodiment, the metal can be one selected from a group consisting of Li, Na, K, Rb, Cs, Mg, Ca, Sr, Ba, La, Ce, Sm, Eu, Tb, Dy, and Yb. In another embodiment, the n-type dopant can be one selected from a group consisting of Cs, K, Rb, Mg, Na, Ca, Sr, Eu and Yb. In an embodiment the alkali metal compound may be 8-Hydroxyquinolinolato-lithium (LiQ), Lithium tetra(1H-pyrazol-1-yl)borate or Lithium 2-(diphenylphosphoryl)phenolate. Suitable compounds for the ETM (which may be used in addition to the inventive compound represented by the general Formula (I) as defined above) are not particularly limited. In one embodiment, the electron transport matrix compounds consist of covalently bound atoms. Preferably, the electron transport matrix compound comprises a conjugated system of at least 6, more preferably of at least 10 delocalized electrons. In one embodiment, the conjugated system of delocalized electrons may be comprised in aromatic or heteroaromatic structural moieties, as disclosed e.g. in documents EP 1 970 371 A1 or WO 2013/079217 A1.

Electron Injection Layer (EIL)

An optional EIL, which may facilitates injection of electrons from the cathode, may be formed on the ETL, preferably directly on the electron transport layer. Examples of materials for forming the EIL include lithium 8-hydroxyquinolinolate (LiQ), LiF, NaCl, CsF, $Li_2O$, BaO, Ca, Ba, Yb, Mg which are known in the art. Deposition and coating conditions for forming the EIL are similar to those for formation of the HIL, although the deposition and coating conditions may vary, according to the material that is used to form the EIL. The EIL may be the organic semiconducting layer comprising the compound of Formula (I).

The thickness of the EIL may be in the range from about 0.1 nm to about 10 nm, for example, in the range from about 0.5 nm to about 9 nm. When the thickness of the EIL is within this range, the EIL may have satisfactory electron-injecting properties, without a substantial penalty in driving voltage.

Cathode Electrode

The cathode electrode is formed on the EIL if present. The cathode electrode may be formed of a metal, an alloy, an electrically conductive compound, or a mixture thereof. The cathode electrode may have a low work function. For example, the cathode electrode may be formed of lithium (Li), magnesium (Mg), aluminum (Al), aluminum (Al)-lithium (Li), calcium (Ca), barium (Ba), ytterbium (Yb), magnesium (Mg)-indium (In), magnesium (Mg)-silver (Ag), or the like. Alternatively, the cathode electrode may be formed of a transparent conductive oxide, such as ITO or IZO.

The thickness of the cathode electrode may be in the range from about 5 nm to about 1000 nm, for example, in the range from about 10 nm to about 100 nm. When the thickness of the cathode electrode is in the range from about 5 nm to about 50 nm, the cathode electrode may be transparent or semitransparent even if formed from a metal or metal alloy.

It is to be understood that the cathode electrode is not part of an electron injection layer or the electron transport layer.

Charge Generation Layer/Hole Generating Layer

The charge generation layer (CGL) may comprise a p-type and an n-type layer. An interlayer may be arranged between the p-type layer and the n-type layer.

Typically, the charge generation layer is a pn junction joining an n-type charge generation layer (electron generating layer) and a hole generating layer. The n-side of the pn junction generates electrons and injects them into the layer which is adjacent in the direction to the anode. Analogously, the p-side of the p-n junction generates holes and injects them into the layer which is adjacent in the direction to the cathode.

Charge generating layers are used in tandem devices, for example, in tandem OLEDs comprising, between two electrodes, two or more emission layers. In a tandem OLED comprising two emission layers, the n-type charge generation layer provides electrons for the first light emission layer arranged near the anode, while the hole generating layer provides holes to the second light emission layer arranged between the first emission layer and the cathode.

Suitable matrix materials for the hole generating layer may be materials conventionally used as hole injection and/or hole transport matrix materials. Also, p-type dopant used for the hole generating layer can employ conventional materials. For example, the p-type dopant can be one selected from a group consisting of tetrafluore-7,7,8,8-tetracyanoquinodimethane (F4-TCNQ), derivatives of tetracyanoquinodimethane, radialene derivatives, iodine, FeCl3, FeF3, and SbCl5. Also, the host can be one selected from a group consisting of N,N'-di(naphthalen-1-yl)-N,N-diphenyl-benzidine (NPB), N,N'-diphenyl-N,N'-bis(3-methylphenyl)-1,1-biphenyl-4,4'-diamine (TPD) and N,N',N'-tetranaphthyl-benzidine (TNB). The p-type charge generation layer may consist of CNHAT.

The n-type charge generating layer may be the layer comprising the compound of Formula (I). The n-type charge generation layer can be layer of a neat n-type dopant, for example of an electropositive metal, or can consist of an organic matrix material doped with the n-type dopant. In one embodiment, the n-type dopant can be alkali metal, alkali metal compound, alkaline earth metal, alkaline earth metal compound, a transition metal, a transition metal compound or a rare earth metal. In another embodiment, the metal can be one selected from a group consisting of Li, Na, K, Rb, Cs, Mg, Ca, Sr, Ba, La, Ce, Sm, Eu, Tb, Dy, and Yb. More specifically, the n-type dopant can be one selected from a group consisting of Cs, K, Rb, Mg, Na, Ca, Sr, Eu and Yb. Suitable matrix materials for the electron generating layer may be the materials conventionally used as matrix materials for electron injection or electron transport layers. The matrix material can be for example one selected from a group consisting of triazine compounds, hydroxyquinoline derivatives like tris(8-hydroxyquinoline)aluminum, benzazole derivatives, and silole derivatives.

The hole generating layer is arranged in direct contact to the n-type charge generation layer.

Organic Light-Emitting Diode (OLED)

The organic electronic device according to the invention may be an organic light-emitting device.

According to one aspect of the present invention, there is provided an organic light-emitting diode (OLED) comprising: a substrate; an anode electrode formed on the substrate; a hole injection layer, a hole transport layer, an emission layer, an organic semiconducting layer comprising a compound of formula (I) and a cathode electrode.

According to another aspect of the present invention, there is provided an OLED comprising: a substrate; an anode electrode formed on the substrate; a hole injection layer, a hole transport layer, an electron blocking layer, an emission layer, a hole blocking layer, an organic semiconducting layer comprising a compound of formula (I) and a cathode electrode.

According to another aspect of the present invention, there is provided an OLED comprising: a substrate; an anode electrode formed on the substrate; a hole injection layer, a hole transport layer, an electron blocking layer, an emission layer, a hole blocking layer, an organic semiconducting layer comprising a compound of Formula (I), an electron injection layer, and a cathode electrode.

According to various embodiments of the present invention, there may be provided OLEDs layers arranged between the above mentioned layers, on the substrate or on the top electrode.

According to one aspect, the OLED can comprise a layer structure of a substrate that is adjacent arranged to an anode electrode, the anode electrode is adjacent arranged to a first hole injection layer, the first hole injection layer is adjacent arranged to a first hole transport layer, the first hole transport layer is adjacent arranged to a first electron blocking layer, the first electron blocking layer is adjacent arranged to a first emission layer, the first emission layer is adjacent arranged to a first electron transport layer, the first electron transport layer is adjacent arranged to an n-type charge generation layer, the n-type charge generation layer is adjacent arranged to a hole generating layer, the hole generating layer is adjacent arranged to a second hole transport layer, the second hole transport layer is adjacent arranged to a second electron blocking layer, the second electron blocking layer is adjacent arranged to a second emission layer, between the second emission layer and the cathode electrode an optional electron transport layer and/or an optional injection layer are arranged.

The organic semiconducting layer according to the invention may be the electron transport layer, first electron transport layer, n-type charge generation layer and/or second electron transport layer.

For example, the OLED according to FIG. 2 may be formed by a process, wherein on a substrate (110), an anode (120), a hole injection layer (130), a hole transport layer (140), an electron blocking layer (145), an emission layer (150), a hole blocking layer (155), an electron transport layer (160), an electron injection layer (180) and the cathode electrode (190) are subsequently formed in that order.

Organic Electronic Device

An organic electronic device according to the invention comprises an organic semiconducting layer comprising a compound according to Formula (I).

An organic electronic device according to one embodiment may include a substrate, an anode layer, an organic semiconducting layer comprising a compound of Formula (I) and a cathode layer.

An organic electronic device according to one embodiment comprises at least one organic semiconducting layer comprising at least one compound of Formula (I), at least one anode layer, at least one cathode layer and at least one emission layer, wherein the organic semiconducting layer is preferably arranged between the emission layer and the cathode layer.

An organic light-emitting diode (OLED) according to the invention may include an anode, a hole transport layer (HTL), an emission layer (EML), an electron transport layer (ETL) comprising at least one compound of Formula (I), and a cathode, which are sequentially stacked on a substrate. In this regard, the HTL, the EML, and the ETL are thin films formed from organic compounds.

An organic electronic device according to one embodiment can be a light emitting device, thin film transistor, a battery, a display device or a photovoltaic cell, and preferably a light emitting device.

According to another aspect of the present invention, there is provided a method of manufacturing an organic electronic device, the method using:
at least one deposition source, preferably two deposition sources and more preferred at least three deposition sources.

The methods for deposition that can be suitable comprise:
deposition via vacuum thermal evaporation;
deposition via solution processing, preferably the processing is selected from spin-coating, printing, casting; and/or
slot-die coating.

According to various embodiments of the present invention, there is provided a method using:
a first deposition source to release the compound of Formula (I) according to the invention, and
a second deposition source to release the metal, a metal salt or an alkali or alkaline earth metal complex; alternatively an organic alkali or alkaline earth metal complex; alternatively 8-hydroxyquinolinolato lithium or alkali borate;
the method comprising the steps of forming the organic semiconducting layer; whereby for an organic light-emitting diode (OLED):
the organic semiconducting layer is formed by releasing the compound of Formula (I) according to the invention from the first deposition source and a metal, a metal salt or an alkali or alkaline earth metal complex; alternatively an organic alkali or alkaline earth metal complex; alternatively 8-hydroxyquinolinolato lithium or alkali borate, from the second deposition source.

According to various embodiments of the present invention, the method may further include forming on the anode electrode, an emission layer and at least one layer selected from the group consisting of forming a hole injection layer, forming a hole transport layer, or forming a hole blocking layer, between the anode electrode and the first electron transport layer.

According to various embodiments of the present invention, the method may further include the steps for forming an organic light-emitting diode (OLED), wherein
on a substrate a first anode electrode is formed,
on the first anode electrode an emission layer is formed,
on the emission layer an electron transport layer stack is formed, optionally a hole blocking layer is formed on the emission layer and an organic semiconducting layer is formed,
and finally a cathode electrode is formed,
optional a hole injection layer, a hole transport layer, and a hole blocking layer, formed in that order between the first anode electrode and the emission layer,
optional an electron injection layer is formed between the organic semiconducting layer and the cathode electrode.

According to various embodiments of the present invention, the method may further comprise forming an electron injection layer on the organic semiconducting layer. However, according to various embodiments of the OLED of the present invention, the OLED may not comprise an electron injection layer.

According to various embodiments, the OLED may have the following layer structure, wherein the layers having the following order:
anode, hole injection layer, first hole transport layer, second hole transport layer, emission layer, optional hole blocking layer, organic semiconducting layer comprising a compound of Formula (I) according to the invention, optional electron injection layer, and cathode.

According to another aspect of the invention, it is provided an electronic device comprising at least one organic light emitting device according to any embodiment described throughout this application, preferably, the electronic device comprises the organic light emitting diode in one of embodiments described throughout this application. More preferably, the electronic device is a display device.

In one embodiment, the organic electronic device according to the invention comprising an organic semiconducting layer comprising a compound according to Formula (I) may further comprise a layer comprising a radialene compound and/or a quinodimethane compound.

In one embodiment, the radialene compound and/or the quinodimethane compound may be substituted with one or more halogen atoms and/or with one or more electron withdrawing groups. Electron withdrawing groups can be selected from nitrile groups, halogenated alkyl groups, alternatively from perhalogenated alkyl groups, alternatively from perfluorinated alkyl groups. Other examples of electron withdrawing groups may be acyl, sulfonyl groups or phosphoryl groups.

Alternatively, acyl groups, sulfonyl groups and/or phosphoryl groups may comprise halogenated and/or perhalogenated hydrocarbyl. In one embodiment, the perhalogenated hydrocarbyl may be a perfluorinated hydrocarbyl. Examples of a perfluorinated hydrocarbyl can be perfluormethyl, perfluorethyl, perfluorpropyl, perfluorisopropyl, perfluorobutyl, perfluorophenyl, perfluorotolyl; examples of sulfonyl groups comprising a halogenated hydrocarbyl may be trifluoromethylsulfonyl, pentafluoroethylsulfonyl, pentafluorophenylsulfonyl, heptafluoropropylsufonyl, nonafluorobutylsulfonyl, and like.

In one embodiment, the radialene and/or the quinodimethane compound may be comprised in a hole injection, hole transporting and/or a hole generation layer.

In one embodiment, the radialene compound may have Formula (XX) and/or the quinodimethane compound may have Formula (XXIa) or (XXIb):

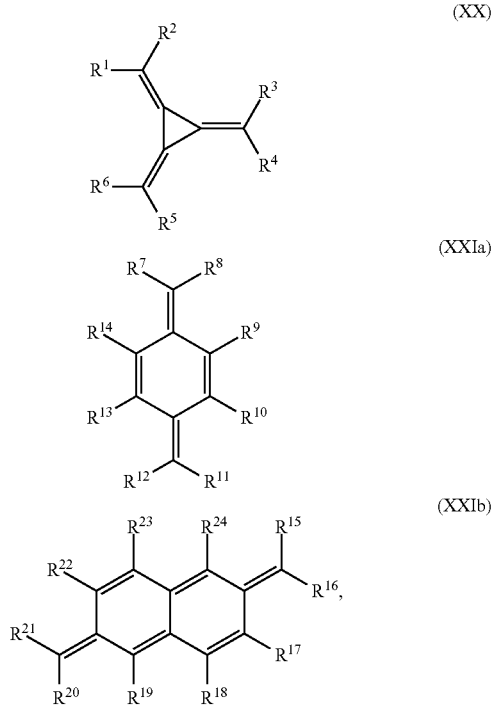

wherein $R^1$, $R^2$, $R^3$, $R^4$, $R^5$, $R^6$, $R^7$, $R^8$, $R^{11}$, $R^{12}$, $R^{15}$, $R^{16}$, $R^{20}$, $R^{21}$ are independently selected from above mentioned electron withdrawing groups and $R^9$, $R^{10}$, $R^{13}$, $R^{14}$, $R^{17}$, $R^{18}$, $R^{19}$, $R^{22}$, $R^{23}$ and $R^{24}$ are independently selected from H, halogen and above mentioned electron withdrawing groups.

Hereinafter, the embodiments are illustrated in more detail with reference to examples. However, the present disclosure is not limited to the following examples. Reference will now be made in detail to the exemplary aspects.

Details and Definitions of the Invention

As explained above, the inventive compound of Formula (I) comprises at least one group of the Formula (II). Each of the groups $R^1$ to $R^{10}$ and/or the group $Ar^4$ may be the group having the Formula (II). However, it may also be provided that only one of these groups has the Formula (II). In Formula (II) the single bond between the asterisk symbol and the group L is the same single bond as that between the respective group R'', respectively $Ar^4$, and the benzoacridine moiety, i.e. the core part of Formula (I) without the groups $R^1$ to $R^{10}$ and $Ar^4$.

The inventive compounds are characterized in that the groups $Ar^2$ and $Ar^3$ are not the same, i.e. are selected differently from each other. These "asymmetrically substituted" compounds show superior properties in comparison with the known "symmetrically substituted" compounds known in the art. Within the group of "asymmetrically substituted" compounds, particular groups of compounds referred to above in detail have been found to be particularly advantageous. Further details are clear when considering the teaching of the specific examples presented below.

The term "system of fused rings" is used herein refers to a binding situation where two of the groups $R^1$ and $R^2$; or $R^2$ and $R^3$; or $R^3$ and $R^4$ form together a first ring fused to the remaining part of the structure having the formula (I) and where, additionally, at least one second ring is fused to the first ring. Likewise, a third ring, a fourth ring etc. may be fused to the first ring or one of the other fused rings of the fused ring system. It may be provided that the total number of carbon atoms comprised on the fused ring system does not exceed 40, alternatively does not exceed 30, alternatively does not exceed 20. An exemplary compound of such a fused ring system is part of the above structure (Id).

In the present specification, when a definition is not otherwise provided, an "alkyl group" may refer to an aliphatic hydrocarbon group. The alkyl group may refer to "a saturated alkyl group" without any double bond or triple bond. The term "alkyl" as used herein shall encompass linear as well as branched and cyclic alkyl. For example, $C_3$-alkyl may be selected from n-propyl and iso-propyl. Likewise, $C_4$-alkyl encompasses n-butyl, sec-butyl and t-butyl. Likewise, $C_6$-alkyl encompasses n-hexyl and cyclohexyl.

The subscribed number n in $C_n$ relates to the total number of carbon atoms in the respective alkyl, arylene, heteroarylene or aryl group.

The term "aryl" or "arylene" as used herein shall encompass phenyl ($C_6$-aryl), fused aromatics, such as naphthalene, anthracene, phenanthracene, tetracene etc. Further encompassed are biphenyl and oligo- or polyphenyls, such as terphenyl etc. Further encompassed shall be any further aromatic hydrocarbon substituents, such as fluorenyl etc. "Arylene" respectively "heteroarylene", refers to groups to which two further moieties are attached. In the present specification the term "aryl group" or "arylene group" may refer to a group comprising at least one hydrocarbon aromatic moiety, and all the elements of the hydrocarbon aromatic moiety may have p-orbitals which form conjugation, for example a phenyl group, a naphtyl group, an anthracenyl group, a phenanthrenyl group, a pyrenyl group, a fluorenyl group and the like. The aryl or arylene group may include a monocyclic or fused ring polycyclic (i.e., rings sharing adjacent pairs of carbon atoms) functional group.

The term "heteroaryl" as used herein refers to aryl groups in which at least one carbon atom is substituted with a heteroatom, preferably selected from N, O, S, B or Si.

The subscripted number n in $C_n$-heteroaryl merely refers to the number of carbon atoms excluding the number of heteroatoms. In this context, it is clear that a $C_3$ heteroarylene group is an aromatic compound comprising three carbon atoms, such as pyrazol, imidazole, oxazole, thiazole and the like.

The term "heteroaryl" may refer to aromatic heterocycles with at least one heteroatom, and all the elements of the hydrocarbon heteroaromatic moiety may have p-orbitals which form conjugation. The heteroatom may be selected from N, O, S, B, Si, P, Se, preferably from N, O and S. A heteroarylene ring may comprise at least 1 to 3 heteroatoms.

Preferably a heteroarylene ring may comprise at least 1 to 3 heteroatoms individually selected from N, S and/or O.

The term "heteroaryl" as used herewith shall encompass pyridine, quinoline, quinazoline, pyridine, triazine, benzimidazole, benzothiazole, benzo[4,5]thieno[3,2-d]pyrimidine, carbazole, xanthene, phenoxazine, benzoacridine, dibenzoacridine and the like.

In the present specification, the single bond refers to a direct bond.

The term "fluorinated" as used herein refers to a hydrocarbon group in which at least one of the hydrogen atoms comprised in the hydrocarbon group is substituted by a fluorine atom.

Fluorinated groups in which all of the hydrogen atoms thereof are substituted by fluorine atoms are referred to as perfluorinated groups and are particularly addressed by the term "fluorinated".

In terms of the invention, a group is "substituted with" another group if one of the hydrogen atoms comprised in this group is replaced by another group, wherein the other group is the substituent.

In terms of the invention, the expression "between" with respect to one layer being between two other layers does not exclude the presence of further layers which may be arranged between the one layer and one of the two other layers. In terms of the invention, the expression "in direct contact" with respect to two layers being in direct contact with each other means that no further layer is arranged between those two layers. One layer deposited on the top of another layer is deemed to be in direct contact with this layer.

With respect to the inventive organic semiconductive layer as well as with respect to the inventive compound, the compounds mentioned in the experimental part are most preferred.

The inventive organic electronic device may be an organic electroluminescent device (OLED) an organic photovoltaic device (OPV), a lighting device, or an organic field-effect transistor (OFET). A lighting device may be any of the devices used for illumination, irradiation, signaling, or projection. They are correspondingly classified as illuminating, irradiating, signaling, and projecting devices. A lighting device usually consists of a source of optical radiation, a device that transmits the radiant flux into space in the desired direction, and a housing that joins the parts into a single device and protects the radiation source and light-transmitting system against damage and the effects of the surroundings.

According to another aspect, the organic electroluminescent device according to the present invention may comprise more than one emission layer, preferably two or three emission layers. An OLED comprising more than one emission layer is also described as a tandem OLED or stacked OLED.

The organic electroluminescent device (OLED) may be a bottom- or top-emission device.

Another aspect is directed to a device comprising at least one organic electroluminescent device (OLED).

A device comprising organic light-emitting diodes is for example a display or a lighting panel.

In the present invention, the following defined terms, these definitions shall be applied, unless a different definition is given in the claims or elsewhere in this specification.

In the context of the present specification the term "different" or "differs" in connection with the matrix material means that the matrix material differs in their structural Formula.

The terms "OLED" and "organic light-emitting diode" are simultaneously used and have the same meaning. The term "organic electroluminescent device" as used herein may comprise both organic light emitting diodes as well as organic light emitting transistors (OLETs).

As used herein, "weight percent", "wt.-%", "percent by weight", "% by weight", and variations thereof refer to a composition, component, substance or agent as the weight of that component, substance or agent of the respective electron transport layer divided by the total weight of the respective electron transport layer thereof and multiplied by 100. It is under-stood that the total weight percent amount of all components, substances and agents of the respective electron transport layer and electron injection layer are selected such that it does not exceed 100 wt.-%.

As used herein, "volume percent", "vol.-%", "percent by volume", "% by volume", and variations thereof refer to a composition, component, substance or agent as the volume of that component, substance or agent of the respective electron transport layer divided by the total volume of the respective electron transport layer thereof and multiplied by 100. It is understood that the total volume percent amount of all components, substances and agents of the cathode layer are selected such that it does not exceed 100 vol.-%.

All numeric values are herein assumed to be modified by the term "about", whether or not explicitly indicated. As used herein, the term "about" refers to variation in the numerical quantity that can occur. Whether or not modified by the term "about" the claims include equivalents to the quantities.

It should be noted that, as used in this specification and the appended claims, the singular forms "a", "an", and "the" include plural referents unless the content clearly dictates otherwise.

The term "free of", "does not contain", "does not comprise" does not exclude impurities. Impurities have no technical effect with respect to the object achieved by the present invention.

In the context of the present specification the term "essentially non-emissive" or "non-emissive" means that the contribution of the compound or layer to the visible emission spectrum from the device is less than 10%, preferably less than 5% relative to the visible emission spectrum. The visible emission spectrum is an emission spectrum with a wavelength of about >380 nm to about <780 nm.

Preferably, the organic semiconducting layer comprising the compound of Formula I is essentially non-emissive or non-emitting.

The operating voltage, also named U, is measured in Volt (V) at 10 milliAmpere per square centimeter (mA/cm2).

The candela per Ampere efficiency, also named cd/A efficiency is measured in candela per ampere at 10 milli-Ampere per square centimeter (mA/cm2).

The external quantum efficiency, also named EQE, is measured in percent (%).

The color space is described by coordinates CIE-x and CIE-y (International Commission on Illumination 1931). For blue emission the CIE-y is of particular importance. A smaller CIE-y denotes a deeper blue color.

The highest occupied molecular orbital, also named HOMO, and lowest unoccupied molecular orbital, also named LUMO, are measured in electron volt (eV).

The term "OLED", "organic light emitting diode", "organic light emitting device", "organic optoelectronic device" and "organic light-emitting diode" are simultaneously used and have the same meaning.

The term "life-span" and "lifetime" are simultaneously used and have the same meaning.

The anode electrode and cathode electrode may be described as anode electrode/cathode electrode or anode electrode/cathode electrode or anode electrode layer/cathode electrode layer.

Room temperature, also named ambient temperature, is 23° C.

BRIEF DESCRIPTION OF THE DRAWINGS

These and/or other aspects and advantages of the present invention will become apparent and more readily appreciated from the following description of the exemplary embodiments, taken in conjunction with the accompanying drawings, of which.

DETAILED DESCRIPTION

Figure 1:
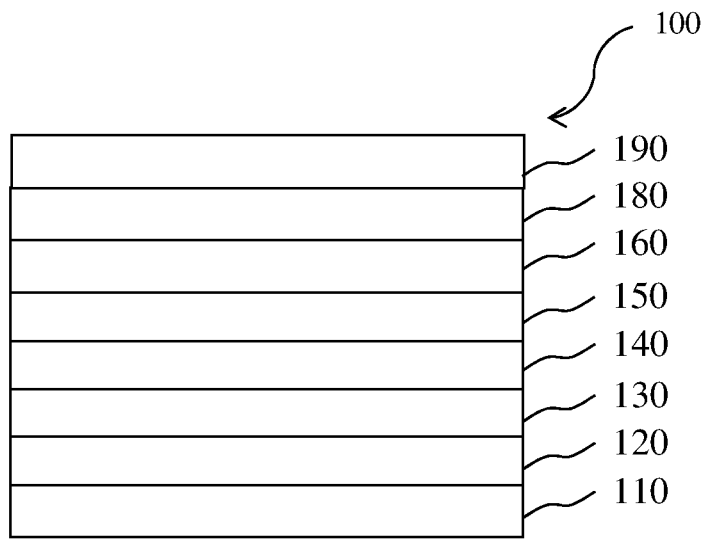
FIG. 1 is a schematic sectional view of an organic light-emitting diode (OLED), according to an exemplary embodiment of the present invention.

Reference will now be made in detail to the exemplary embodiments of the present invention, examples of which are illustrated in the accompanying drawings, wherein like reference numerals refer to the like elements throughout. The exemplary embodiments are described below, in order to explain the aspects of the present invention, by referring to the figures.

Herein, when a first element is referred to as being formed or disposed "on" or "onto" a second element, the first element can be disposed directly on the second element, or one or more other elements may be disposed there between. When a first element is referred to as being formed or disposed "directly on" or "directly onto" a second element, no other elements are disposed there between.

FIG. 1 is a schematic sectional view of an organic light-emitting diode (OLED) 100, according to an exemplary embodiment of the present invention. The OLED 100 includes a substrate 110, an anode 120, a hole injection layer (HIL) 130, a hole transport layer (HTL) 140, an emission layer (EML) 150, an electron transport layer (ETL) 160. The electron transport layer (ETL) 160 is formed on the EML 150. Onto the electron transport layer (ETL) 160, an electron injection layer (EIL) 180 is disposed. The cathode 190 is disposed directly onto the electron injection layer (EIL) 180.

Instead of a single electron transport layer 160, optionally an electron transport layer stack (ETL) can be used.

Figure 2:
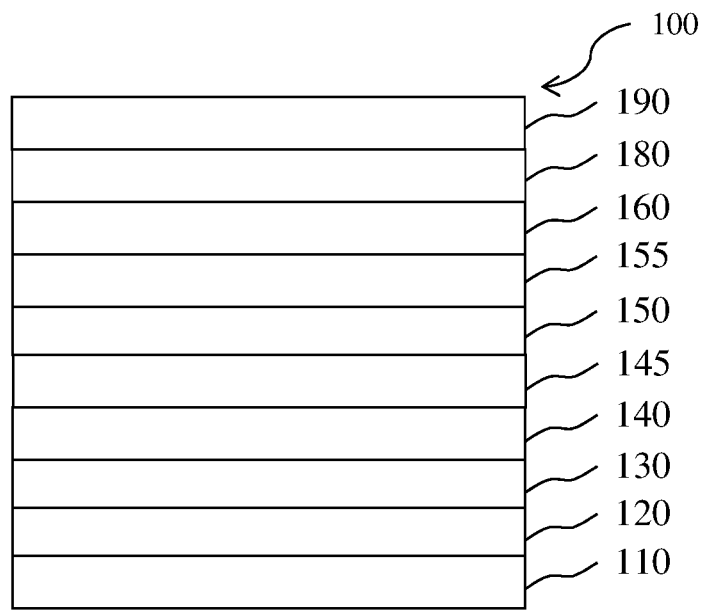
FIG. 2 is a schematic sectional view of an OLED, according to an exemplary embodiment of the present invention.

FIG. 2 is a schematic sectional view of an OLED 100, according to another exemplary embodiment of the present invention. FIG. 2 differs from FIG. 1 in that the OLED 100 of FIG. 2 comprises an electron blocking layer (EBL) 145 and a hole blocking layer (HBL) 155.

Referring to FIG. 2, the OLED 100 includes a substrate 110, an anode 120, a hole injection layer (HIL) 130, a hole transport layer (HTL) 140, an electron blocking layer (EBL) 145, an emission layer (EML) 150, a hole blocking layer (HBL) 155, an electron transport layer (ETL) 160, an electron injection layer (EIL) 180 and a cathode electrode 190.

Preferably, the organic semiconducting layer comprising a compound of Formula (I) may be an ETL.

Figure 3:
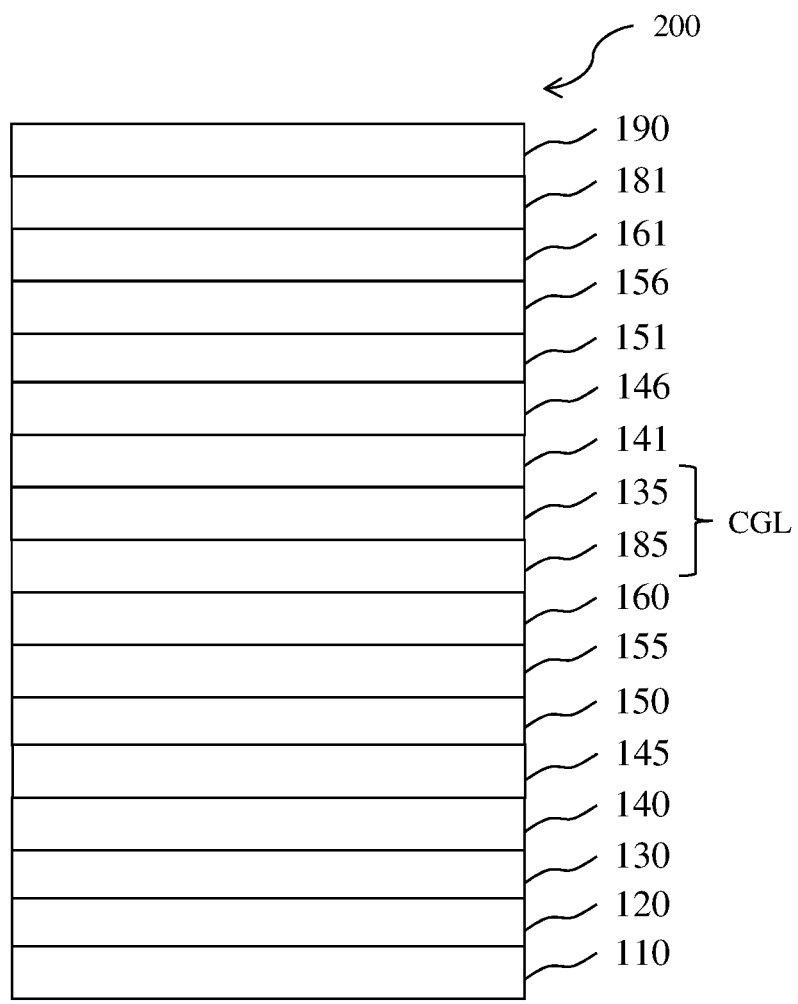
FIG. 3 is a schematic sectional view of a tandem OLED comprising a charge generation layer, according to an exemplary embodiment of the present invention.

FIG. 3 is a schematic sectional view of a tandem OLED 200, according to another exemplary embodiment of the present invention. FIG. 3 differs from FIG. 2 in that the OLED 100 of FIG. 3 further comprises a charge generation layer (CGL) and a second emission layer (151).

Referring to FIG. 3, the OLED 200 includes a substrate 110, an anode 120, a first hole injection layer (HIL) 130, a first hole transport layer (HTL) 140, a first electron blocking layer (EBL) 145, a first emission layer (EML) 150, a first hole blocking layer (HBL) 155, a first electron transport layer (ETL) 160, an n-type charge generation layer (n-type CGL) 185, a hole generating layer (p-type charge generation layer; p-type GCL) 135, a second hole transport layer (HTL) 141, a second electron blocking layer (EBL) 146, a second emission layer (EML) 151, a second hole blocking layer (EBL) 156, a second electron transport layer (ETL) 161, a second electron injection layer (EIL) 181 and a cathode 190.

Preferably, the organic semiconducting layer comprising a compound of Formula (I) may be the first ETL, n-type CGL and/or second ETL.

While not shown in FIG. 1, FIG. 2 and FIG. 3, a sealing layer may further be formed on the cathode electrodes 190, in order to seal the OLEDs 100 and 200. In addition, various other modifications may be applied thereto.

Hereinafter, one or more exemplary embodiments of the present invention will be described in detail with, reference to the following examples. However, these examples are not intended to limit the purpose and scope of the one or more exemplary embodiments of the present invention.

Experimental Data

Preparation of Compounds of Formula (I)

Compounds of formula (I) may be prepared as described below.

Potassium carbonate (20 mmol, 2 eq.) is dissolved in ~10 ml of deionized water, the solution is degassed with $N_2$ for 30 min. Dioxane (40 ml) is degassed in a 100 mL 3-necked round bottom flask with $N_2$ for 30 min. The flask is then charged with corresponding aryl boronic ester (10 mmol, 1 eq.), chlorotriazine (22 mmol, 1.1 eq.) and tetrakis(triphenylphosphin)palladium(0) (0.2 mmol, 0.02 eq.) under a positive nitrogen pressure. The degassed potassium carbonate solution is added using a syringe, nitrogen purged reflux condenser is attached to the flask and a reaction mixture heated to 90° C. with stirring for 12 h. The mixture is allowed to cool down to the room temperature, a precipitate is collected by filtration, washed with water, methanol, dried in vacuum at 40° C. to give a crude product, which could be further purified by re-crystallization or trituration with appropriate solvents. Final purification is achieved by sublimation in a high vacuum.

| Starting materials and products | | |
|---|---|---|
| Aryl boronic ester and chlorotriazine | Product | Yield and MS data |
| | | 52%<br>663<br>[M + H]⁺ |
| | | 89%<br>663<br>[M + H]⁺ |
| | | 78%<br>663<br>[M + H]⁺ |

-continued
Starting materials and products
| Aryl boronic ester and chlorotriazine | Product | Yield and MS data |
|---|---|---|
| 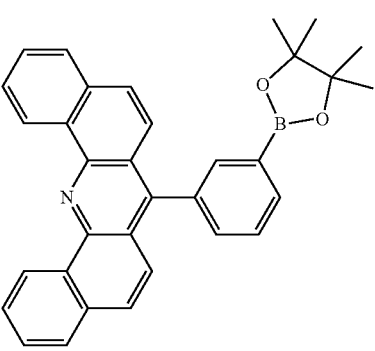 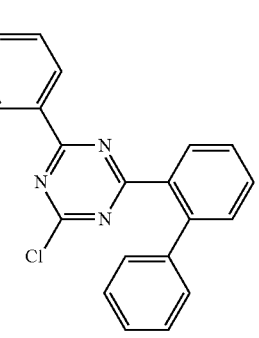 | 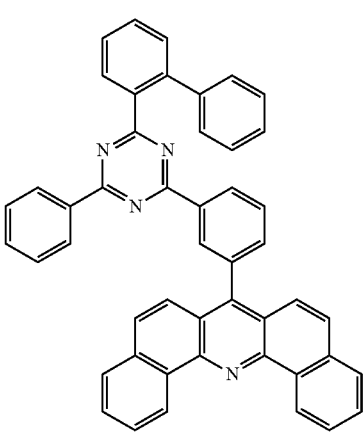 | 69% 663 [M + H]⁺ |
| 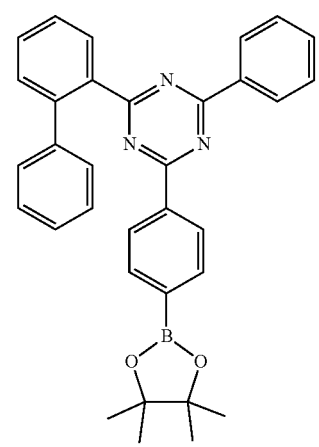 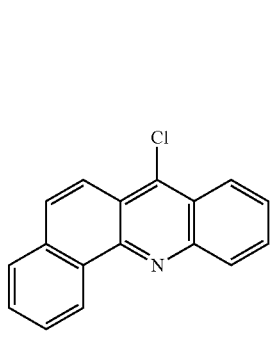 | 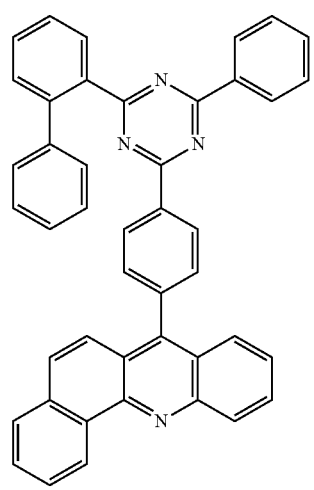 [SMILES: c1ccc(-c2nc(-c3ccc(-c4c5ccccc5nc5c4ccc4ccccc45)cc3)nc(-c3ccccc3-c3ccccc3)n2)cc1] | 66% 613 [M + H]⁺ |
| 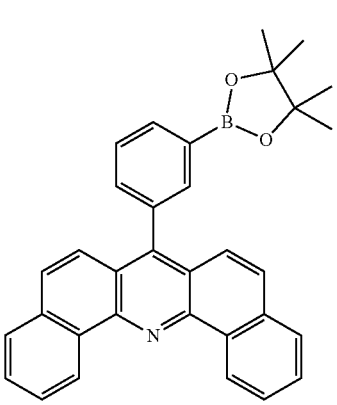 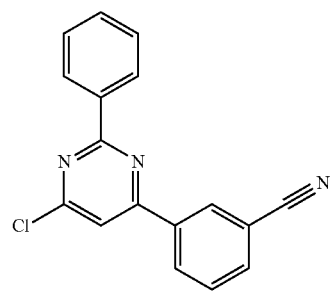 | 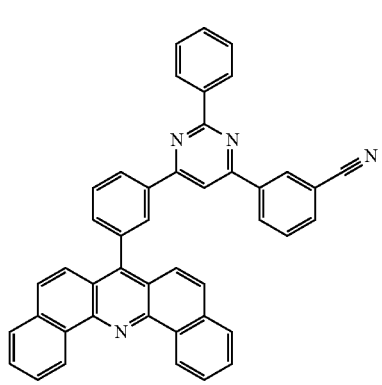 [SMILES: N#Cc1cccc(-c2cc(-c3cccc(-c4c5ccc6ccccc6c5nc5c4ccc4ccccc45)c3)nc(-c3ccccc3)n2)c1] | 38% 611 [M + H]⁺ |

Melting Point

The melting point (mp) is determined as peak temperatures from the DSC curves of the above TGA-DSC measurement or from separate DSC measurements (Mettler Toledo DSC822e, heating of samples from room temperature to completeness of melting with heating rate 10 K/min under a stream of pure nitrogen. Sample amounts of 4 to 6 mg are placed in a 40 µL Mettler Toledo aluminum pan with lid, a <1 mm hole is pierced into the lid).

The melting point of a compound of Formula (I) may be selected in the range of about 260 to about 350° C., preferably about 270 to about 330° C., also preferred about 280 to about 320° C.

Glass Transition Temperature

The glass transition temperature (Tg) is measured under nitrogen and using a heating rate of 10 K per min in a Mettler Toledo DSC 822e differential scanning calorimeter as described in DIN EN ISO 11357, published in March 2010.

The glass transition temperature of a compound of Formula (I) may be selected in the range of about 115 to about 200° C., preferably about 120 to about 190° C., also preferred about 125 to about 180° C.

Reduction Potential

The reduction potential is determined by cyclic voltammetry with potenioststic device Metrohm PGSTAT30 and software Metrohm Autolab GPES at room temperature. The redox potentials given at particular compounds were measured in an argon de-aerated, dry 0.1M THF solution of the tested substance, under argon atmosphere, with 0.1M tetrabutylammonium hexafluorophosphate supporting electrolyte, between platinum working electrodes and with an Ag/AgCl pseudo-standard electrode (Metrohm Silver rod electrode), consisting of a silver wire covered by silver chloride and immersed directly in the measured solution, with the scan rate 100 mV/s. The first run was done in the broadest range of the potential set on the working electrodes, and the range was then adjusted within subsequent runs appropriately. The final three runs were done with the addition of ferrocene (in 0.1M concentration) as the standard. The average of potentials corresponding to cathodic and anodic peak of the studied compound, after subtraction of the average of cathodic and anodic potentials observed for the standard Fc+/Fc redox couple, afforded finally the values reported above. All studied compounds as well as the reported comparative compounds showed well-defined reversible electrochemical behaviour.

Rate Onset Temperature

The rate onset temperature ($T_{RO}$) is determined by loading 100 mg compound into a VTE source. As VTE source a point source for organic materials is used as supplied by Kurt J. Lesker Company (www.lesker.com) or CreaPhys GmbH (http://www.creaphys.com). The VTE source is heated at a constant rate of 15 K/min at a pressure of less than $10^{-5}$ mbar and the temperature inside the source measured with a thermocouple. Evaporation of the compound is detected with a QCM detector which detects deposition of the compound on the quartz crystal of the detector. The deposition rate on the quartz crystal is measured in Ångstrom per second. To determine the rate onset temperature, the deposition rate is plotted against the VTE source temperature. The rate onset is the temperature at which noticeable deposition on the QCM detector occurs. For accurate results, the VTE source is heated and cooled three time and only results from the second and third run are used to determine the rate onset temperature.

To achieve good control over the evaporation rate of an organic compound, the rate onset temperature may be in the range of 200 to 255° C. If the rate onset temperature is below 200° C. the evaporation may be too rapid and therefore difficult to control. If the rate onset temperature is above 255° C. the evaporation rate may be too low which may result in low tact time and decomposition of the organic compound in VTE source may occur due to prolonged exposure to elevated temperatures.

The rate onset temperature is an indirect measure of the volatility of a compound. The higher the rate onset temperature the lower is the volatility of a compound.

The rate onset temperature of a compound of Formula (I) may be selected in the range of about 230 to about 300° C., preferably about 240 to about 290° C.

Dipole Moment

The dipole moment $|\vec{\mu}|$ of a molecule containing N atoms is given by:

$$\vec{\mu} = \sum_i^N q_i \vec{r_i}$$

$$|\vec{\mu}| = \sqrt{\mu_x^2 + \mu_y^2 + \mu_z^2}$$

where $q_i$ and $\vec{r}_i$ are the partial charge and position of atom i in the molecule.

The dipole moment is determined by a semi-empirical molecular orbital method.

The geometries of the molecular structures are optimized using the hybrid functional B3LYP with the 6-31G* basis set in the gas phase as implemented in the program package TURBOMOLE V6.5 (TURBOMOLE GmbH, Litzenhardtstrasse 19, 76135 Karlsruhe, Germany). If more than one conformation is viable, the conformation with the lowest total energy is selected to determine the bond lengths of the molecules.

The dipole moment of a compound of Formula (I) may be selected in the range of about 3 to about 6 Debye, preferably about 3.2 to about 6 Debye, also preferred about 3.4 to about 6 Debye.

HOMO and LUMO

The HOMO and LUMO are calculated with the program package TURBOMOLE V6.5. The optimized geometries and the HOMO and LUMO energy levels of the molecular structures are determined by applying the hybrid functional B3LYP with a 6-31G* basis set in the gas phase. If more than one conformation is viable, the conformation with the lowest total energy is selected.

The HOMO of a compound of Formula (I) may be selected in the range of about −5.4 to about −5.9 eV, preferably about −5.5 to about −5.8 eV, also preferred about −5.6 to about −5.7 eV.

The LUMO of a compound of Formula (I) may be selected in the range of about −1.8 to about −2.1 eV, preferably about −1.85 to about −2.08 eV, also preferred about −1.9 to about −2.05 eV.

General Procedure for Fabrication of OLEDs

For top emission OLED devices, examples 1 to 5 and comparative example 1, a glass substrate was cut to a size of 50 mm×50 mm×0.7 mm, ultrasonically cleaned with isopropyl alcohol for 5 minutes and then with pure water for 5 minutes, and cleaned again with UV ozone for 30 minutes, to prepare the substrate. 100 nm Ag were deposited on the substrate at a pressure of $10^{-5}$ to $10^{-7}$ mbar to form an anode.

Then, 92 vol.-% Biphenyl-4-yl(9,9-diphenyl-9H-fluoren-2-yl)-[4-(9-phenyl-9H-carbazol-3-yl)phenyl]-amine (CAS 1242056-42-3) with 8 vol.-% 2,2',2"-(cyclopropane-1,2,3-triylidene)tris(2-(p-cyanotetrafluorophenyl)acetonitrile) was vacuum deposited on the anode, to form a hole injection layer (HIL) having a thickness of 10 nm. Then, Biphenyl-4-yl(9,9-diphenyl-9H-fluoren-2-yl)-[4-(9-phenyl-9H-carbazol-3-yl)phenyl]-amine was vacuum deposited on the HIL, to form a hole transport layer (HTL) having a thickness of 118 nm.

Then, N,N-bis(4-(dibenzo[b,d]furan-4-yl)phenyl)-[1,1':4',1"-terphenyl]-4-amine (CAS 1198399-61-9) was vacuum deposited on the HTL, to form an electron blocking layer (EBL) having a thickness of 5 nm.

Then, the emission layer (EML) was deposited. 97 vol.-% H09 (Sun Fine Chemicals, South Korea) as EML host and 3 vol.-% BD200 (Sun Fine Chemicals, South Korea) as fluorescent blue dopant were deposited on the EBL, to form a blue-emitting EML with a thickness of 20 nm.

Then, 2,4-diphenyl-6-(4',5',6'-triphenyl-[1,1':2',1":3",1'":3'",1""-quinquephenyl]-3""-yl)-1,3,5-triazine was deposited on the EML, to form a hole blocking layer (HBL) with a thickness of 5 nm.

Then, the electron transport layer (ETL) is formed on the hole blocking layer with a thickness of 31 nm by co-deposition of a matrix compound and an alkali organic complex. The composition of the ETL is shown in Table 2.

Then, the electron injection layer (EIL) is formed on the electron transporting layer by deposing Yb with a thickness of 2 nm.

Ag is evaporated at a rate of 0.01 to 1 Å/s at $10^{-7}$ mbar to form a cathode with a thickness of 11 nm.

A cap layer of Biphenyl-4-yl(9,9-diphenyl-9H-fluoren-2-yl)-[4-(9-phenyl-9H-carbazol-3-yl)phenyl]-amine is formed on the cathode with a thickness of 75 nm.

The OLED stack is protected from ambient conditions by encapsulation of the device with a glass slide. Thereby, a cavity is formed, which includes a getter material for further protection.

To assess the performance of the inventive examples compared to the prior art, the current efficiency is measured at 20° C. The current-voltage characteristics are determined using a Keithley 2635 source measure unit by sourcing a voltage in V and measuring the current in mA flowing through the device under test. The voltage applied to the device is varied in steps of 0.1V in the range between 0V and 10V. Likewise, the luminance-voltage characteristics and CIE coordinates are determined by measuring the luminance in cd/m² using an Instrument Systems CAS-140CT array spectrometer, which has been calibrated by Deutsche Akkreditierungsstelle (DAkkS) for each of the voltage values. The cd/A efficiency at 10 mA/cm² is determined by interpolating the luminance-voltage and current-voltage characteristics, respectively.

Lifetime LT of the device is measured at ambient conditions (20° C.) and 30 mA/cm², using a Keithley 2400 sourcemeter, and recorded in hours.

The brightness of the device is measured using a calibrated photo diode. The lifetime LT is defined as the time till the brightness of the device is reduced to 97% of its initial value.

Technical Effect of the Invention

Properties of Compounds of Formula (I)

In Table 1 are shown mp, $T_g$, $T_{RO}$, HOMO and LUMO energy levels and the dipole moments of comparative compound 1 and compounds of the Formula (I). Surprisingly, compounds of Formula (I) have lower melting points compared to comparative compound 1. Additionally, compounds of Formula (I) have glass transition temperatures in a range suitable for applications in organic electronics. The glass transition temperature should not be too low, as this may affect stability of the organic electronic device, in particular at elevated temperatures, for example for applications in the automobile sector. Additionally, the rate onset temperature of compounds of Formula (I) is in a range suitable for mass production.

Surprisingly, the LUMO of compounds of formula (I) is less negative than the LUMO of comparative compounds 1. Thereby, fine-tuning of charge balance in an organic electronic device may be achieved.

In Table 2 are shown the composition of the organic semiconducting layer, operating voltage, cd/A efficiency and lifetime of comparative example 1 and Examples 1 to 5.

In comparative example 1, the organic semiconducting layer comprises a compound known in the art as matrix compound and LiQ as dopant.

In Examples 1 to 5, the organic semiconducting layer comprises a compound of formula (I) as matrix compound and LiQ as dopant.

As can be seen in Table 2, the operating voltage in Examples 1 to 5 is lower compared to comparative example 1. The cd/A efficiency is improved over comparative example 1. Lower operating voltage and higher cd/A efficiency may result in reduced power consumption. In mobile displays the battery life may be improved. Additionally, the lifetime is improved for Example 1 and 2 compared to comparative example 1. Improved lifetime is important for the long-term stability of a device.

In summary, compounds of Formula (I) and organic electronic devices comprising an organic semiconducting layer comprising of compound of Formula (I) show superior performance over the state of the art.

TABLE 1

Properties of comparative compound 1 and compounds of Formula (I)

| Referred to as: | Structure | mp (° C.) | Tg (° C.) | T$_{RO}$ (° C.) | HOMO (eV) | LUMO (eV) | Dipole moment (Debye) |
|---|---|---|---|---|---|---|---|
| Comparative compound 1 | 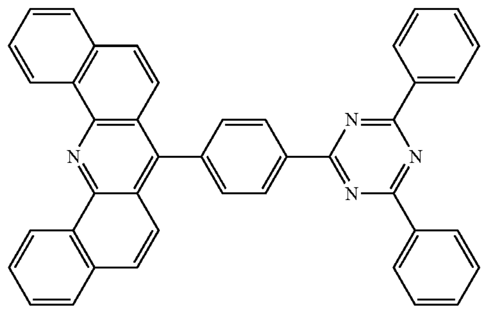 [SMILES: c1ccc(-c2nc(-c3ccccc3)nc(-c3ccc(-c4c5ccc6ccccc6c5nc5c4ccc4ccccc45)cc3)n2)cc1] | 374 | n.d. | 268 | −5.66 | −2.02 | 1.89 |
| A-1 | 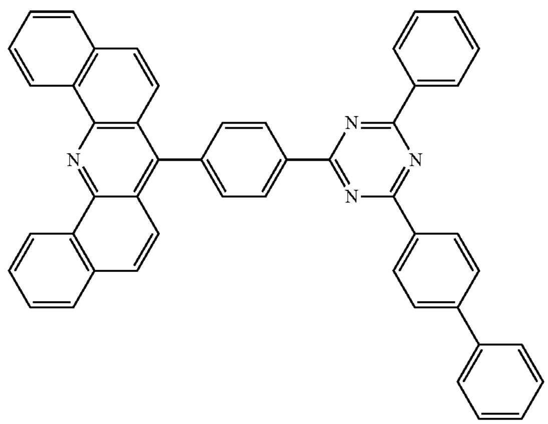 [SMILES: c1ccc(-c2ccc(-c3nc(-c4ccccc4)nc(-c4ccc(-c5c6ccc7ccccc7c6nc6c5ccc5ccccc56)cc4)n3)cc2)cc1] | 333 | 162 | 305 | −5.66 | −2.00 | 2.19 |
| A-2 | 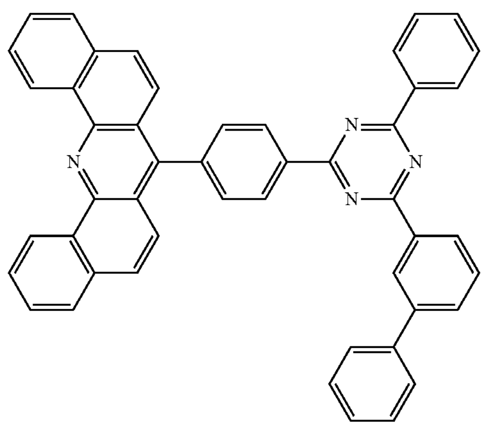 [SMILES: c1ccc(-c2cccc(-c3nc(-c4ccccc4)nc(-c4ccc(-c5c6ccc7ccccc7c6nc6c5ccc5ccccc56)cc4)n3)c2)cc1] | 317 | 148 | 286 | −5.66 | −2.00 | 1.77 |
| A-3 | 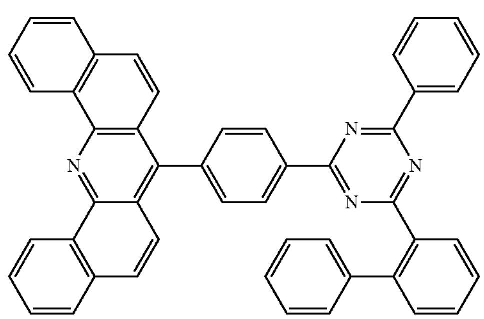 [SMILES: c1ccc(-c2nc(-c3ccc(-c4c5ccc6ccccc6c5nc5c4ccc4ccccc45)cc3)nc(-c3ccccc3-c3ccccc3)n2)cc1] | 290 | 135 | 256 | −5.65 | −1.95 | 2.10 |

TABLE 1-continued
Properties of comparative compound 1 and compounds of Formula (I)
| Referred to as: | Structure | mp (° C.) | Tg (° C.) | $T_{RO}$ (° C.) | HOMO (eV) | LUMO (eV) | Dipole moment (Debye) |
|---|---|---|---|---|---|---|---|
| A-12 | 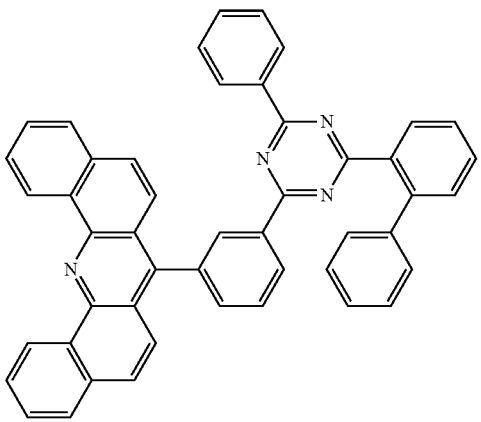 [SMILES: c1ccc(-c2nc(-c3cccc(-c4c5ccc6ccccc6c5nc5c4ccc4ccccc45)c3)nc(-c3ccccc3-c3ccccc3)n2)cc1] | 284 | 133 | 246 | −5.65 | −1.86 | 1.61 |
| A-14 | 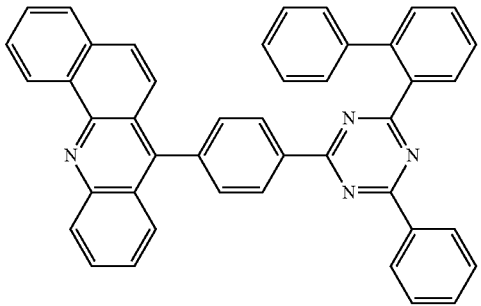 [SMILES: c1ccc(-c2nc(-c3ccc(-c4c5ccccc5nc5c4ccc4ccccc45)cc3)nc(-c3ccccc3-c3ccccc3)n2)cc1] | 206 | 116 | 232 | −5.60 | −2.01 | 2.40 |
| A-15 | 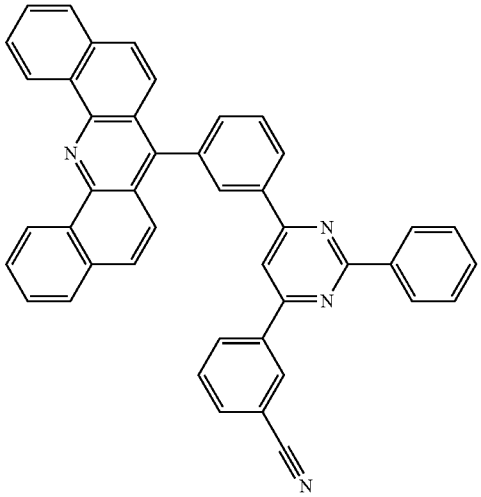 [SMILES: N#Cc1cccc(-c2cc(-c3cccc(-c4c5ccc6ccccc6c5nc5c4ccc4ccccc45)c3)nc(-c3ccccc3)n2)c1] | 340 | 150 | 290 | — | — | — |
n.d. = not measurable

TABLE 2

Performance of an organic electroluminescent device comprising an electron transport layer comprising a matrix compound and an alkali metal complex.

| | Matrix compound | Concentration of matrix compound (vol.-%) in the ETL | Alkali metal complex | Concentration of alkali metal complex (vol.-%) in the ETL | Thickness of the ETL (nm) | Operating voltage at 10 mA/cm$^2$ (V) | cd/A efficiency at 10 mA/cm$^2$ (cd/A) | LT97 at 30 mA/cm$^2$ (h) |
|---|---|---|---|---|---|---|---|---|
| Comparative example 1 | Comparative compound 1 | 50 | LiQ | 50 | 31 | 3.65 | 7.3 | 238 |
| Example 1 | A-2 | 50 | LiQ | 50 | 31 | 3.6 | 7.4 | 280 |
| Example 2 | A-3 | 50 | LiQ | 50 | 31 | 3.6 | 7.5 | 256 |
| Example 3 | A-12 | 50 | LiQ | 50 | 31 | 3.4 | 7.3 | — |
| Example 4 | A-14 | 50 | LiQ | 50 | 31 | 3.6 | 7.3 | — |
| Example 5 | A-15 | 50 | LiQ | 50 | 31 | 3.55 | 7.3 | — |

The features disclosed in the foregoing description and in the dependent claims may, both separately and in any combination thereof, be material for realizing the aspects of the disclosure made in the independent claims, in diverse forms thereof.

We claim:

1. Compound of the Formula (I)

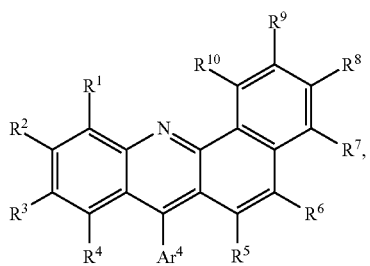

(I)

wherein at least one of $R^1$ to $R^{10}$ and/or $Ar^4$ is a group having the Formula (II)

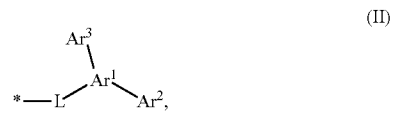

(II)

wherein the asterisk symbol "*" in Formula (II) represents the position of binding of the group having the Formula (II);

L is selected from substituted or unsubstituted $C_6$ to $C_{18}$ arylene;

$Ar^1$ is selected from substituted or unsubstituted $C_3$ to $C_{24}$ heteroaryl, wherein the heteroaryl comprises at least two N-atoms;

$Ar^2$ and $Ar^3$ are independently selected from substituted or unsubstituted $C_6$ to $C_{24}$ aryl and/or substituted or unsubstituted $C_4$ to $C_{24}$ heteroaryl, wherein $Ar^2$ and $Ar^3$ are selected differently from each other;

$Ar^4$ is selected from the group consisting of substituted or unsubstituted $C_1$ to $C_{16}$ alkyl, substituted or unsubstituted $C_6$ to $C_{24}$ aryl, substituted or unsubstituted $C_2$ to $C_{24}$ heteroaryl and a group having the general Formula (II);

$R^1$ to $R^{10}$ are independently selected from the group consisting of H, D, F, $C_1$ to $C_{20}$ alkyl, $C_6$ to $C_{20}$ aryl, $C_2$ to $C_{20}$ heteroaryl and a group having the Formula (II); and $R^1$ and $R^2$; or $R^2$ and $R^3$; or $R^3$ and $R^4$; or $R^5$ and $R^6$ may independently from each other form a fused ring or a system of fused rings;

wherein, in the respective substituted groups, the substituents each are independently selected from the group consisting of D, F, $C_1$ to $C_{20}$ linear alkyl, $C_3$ to $C_{20}$ branched alkyl, $C_3$ to $C_{20}$ cyclic alkyl, $C_1$ to $C_{20}$ linear alkoxy, $C_3$ to $C_{20}$ branched alkoxy, $C_1$ to $C_{12}$ linear fluorinated alkyl, $C_1$ to $C_{12}$ linear fluorinated alkoxy, $C_3$ to $C_{12}$ branched fluorinated cyclic alkyl, $C_3$ to $C_{20}$ fluorinated cyclic alkyl, $C_3$ to $C_{12}$ fluorinated cyclic alkoxy, CN, RCN, $C_6$ to $C_{20}$ aryl, $C_2$ to $C_{20}$ heteroaryl, OR, SR, (C=O)R, (C=O)NR$_2$, SiR$_3$, (S=O)R, (S=O)$_2$R, (P=O)R$_2$; wherein each R is independently selected from the group consisting of $C_1$ to $C_{20}$ linear alkyl, $C_1$ to $C_{20}$ alkoxy, $C_1$ to $C_{20}$ thioalkyl, $C_3$ to $C_{20}$ branched alkyl, $C_3$ to $C_{20}$ cyclic alkyl, $C_3$ to $C_{20}$ branched alkoxy, $C_3$ to $C_{20}$ cyclic alkoxy, $C_3$ to $C_{20}$ branched thioalkyl, $C_3$ to $C_{20}$ cyclic thioalkyl, $C_6$ to $C_{20}$ aryl and $C_2$ to $C_{20}$ heteroaryl.

2. Compound according to claim 1, wherein L is selected from the group consisting of phenylene, biphenylene, terphenylene, phenanthrylene, triphenylylene, and naphthylene.

3. Compound according to claim 1, wherein $Ar^1$ is triazine or pyrimidine.

4. Compound according to claim 1, wherein $Ar^3$ is biphenyl, naphthyl, dibenzofuranyl, or dibenzothiophenyl.

5. Compound according to claim 1, wherein $Ar^2$ is phenyl.

6. Compound according to claim 1, wherein $Ar^4$ is selected from the group consisting of phenyl, biphenyl, terphenyl, naphthyl, and a group having the Formula (II).

7. Compound according to claim 1, wherein $R^1$ and $R^2$ form together a fused ring.

8. Compound according to claim 1, wherein the compound of Formula (I) has one of the following Formulas (Ia), (Ib), (Ic) and (Id):

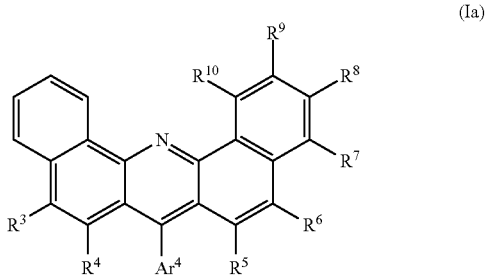

(Ia)

(Ib)
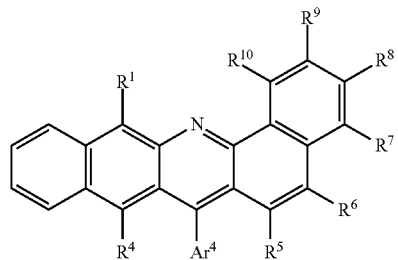
(Ic)
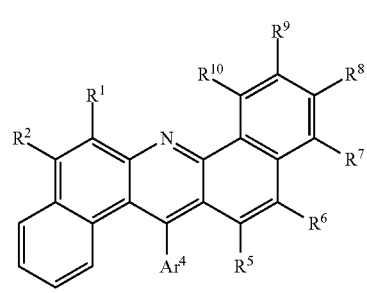
(Id)
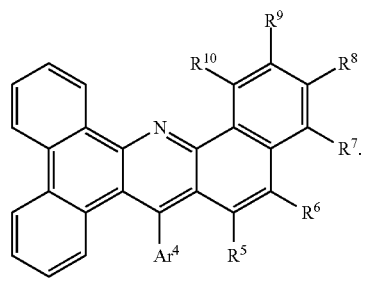
9. Compound according to claim 1, wherein the compound has one of the following structures A-1 to A-15:
A-1
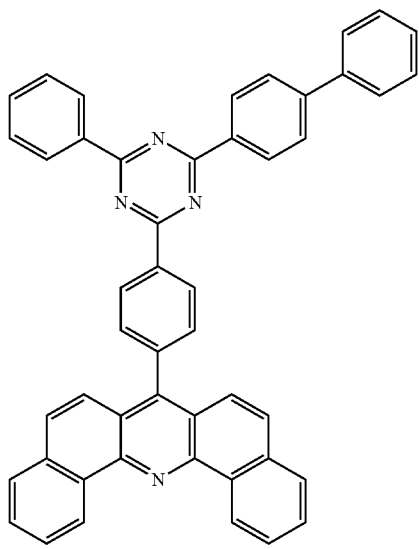
A-2
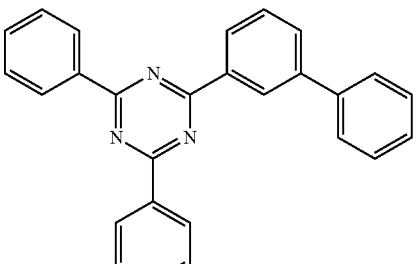
A-3
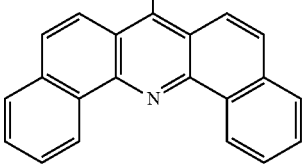
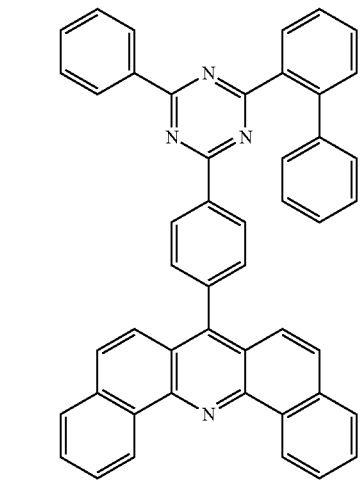
A-4
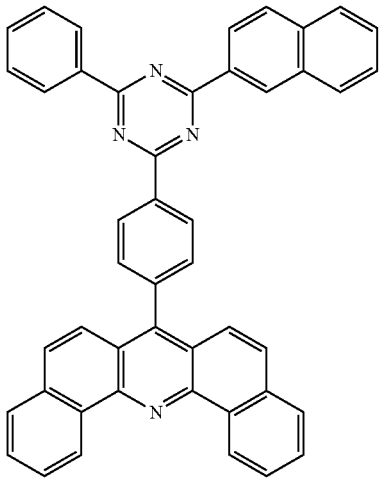

-continued
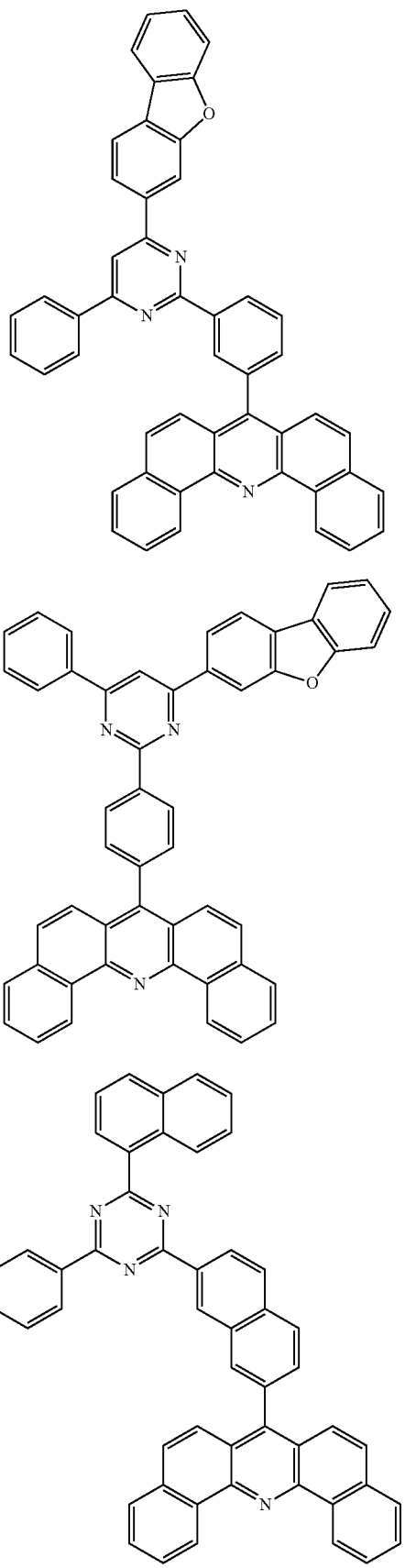
A-5
A-6
A-7
A-8
A-9

A-10
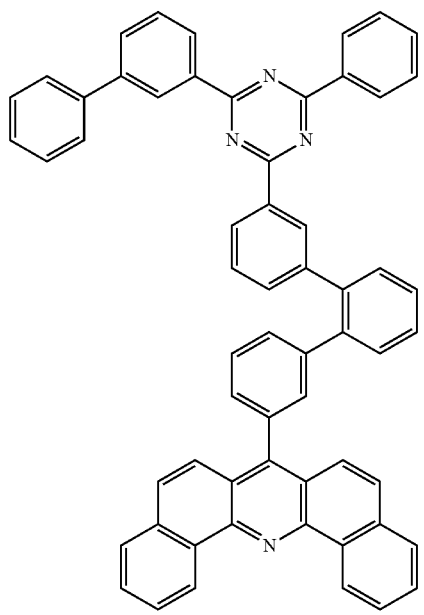
A-11
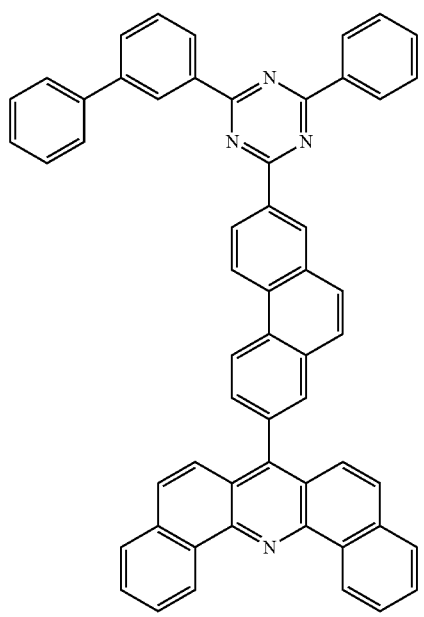
A-12
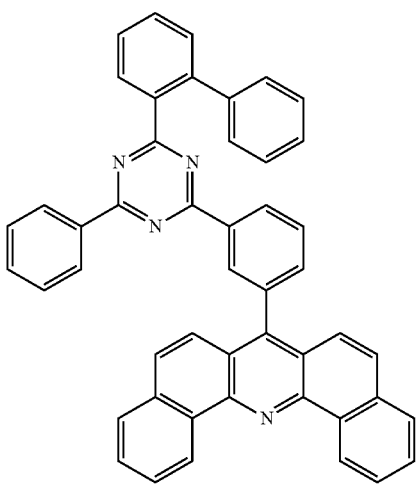
A-13
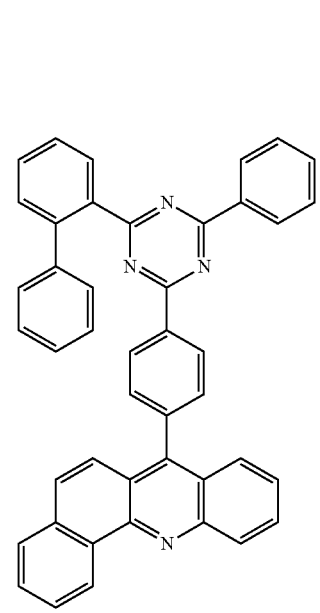
A-14

-continued

A-15

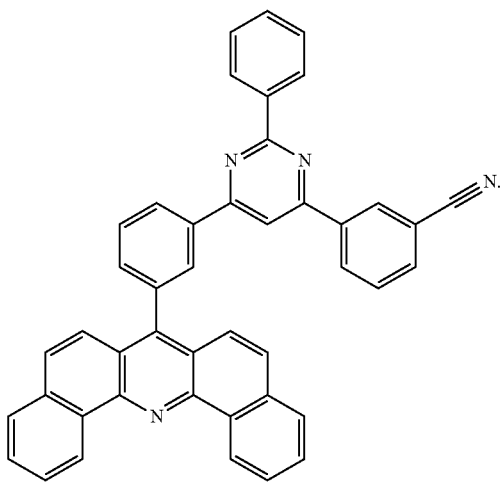

10. Organic semiconducting layer comprising a compound of Formula (I) according to claim 1.

11. Organic semiconducting layer according to claim 10, wherein the organic semiconducting layer further comprises a metal, a metal salt, or an alkali or alkaline earth metal complex.

12. Organic semiconducting layer according to claim 11, wherein the alkali or alkaline earth metal complex is an organic alkali or alkaline earth metal complex.

13. Organic semiconducting layer according to claim 10, wherein the organic semiconducting layer further comprises 8-hydroxyquinolinolato lithium or alkali borate.

14. Organic electronic device comprising an organic semiconducting layer according to claim 10.

15. Organic electronic device according to claim 14 further comprising an anode, an emission layer, and a cathode, wherein the organic semiconducting layer is arranged between the emission layer and the cathode.

16. Display device comprising the organic electronic device according to claim 14.

17. Lighting device comprising the organic electronic device according to claim 14.

* * * * *